United States Patent [19]
Cohen et al.

[11] Patent Number: 5,814,486
[45] Date of Patent: Sep. 29, 1998

[54] HERPES SIMPLEX VIRUS GLYCOPROTEIN D VARIANTS

[75] Inventors: Gary H. Cohen, Havertown, Pa.; Roselyn T. Eisenberg, Haddonfield, N.J.; Anthony Nicola, Philadelphia, Pa.

[73] Assignee: Competitive Technologies, Inc., Westport, Conn.

[21] Appl. No.: 793,958

[22] PCT Filed: Jul. 3, 1996

[86] PCT No.: PCT/US96/11344

§ 371 Date: May 7, 1997

§ 102(e) Date: May 7, 1997

[87] PCT Pub. No.: WO97/03199

PCT Pub. Date: Jan. 30, 1997

[30] Foreign Application Priority Data

Jul. 7, 1995 [EP] European Pat. Off. .............. 08499568

[51] Int. Cl.$^6$ ............................ C12P 21/02; C07K 14/03; C12N 15/38; C12N 5/10

[52] U.S. Cl. .................... 435/69.3; 435/348; 435/252.3; 435/320.1; 435/235.1; 435/365; 530/350; 536/23.72; 930/224; 424/186.1

[58] Field of Search ............................... 435/69.3, 5, 239, 435/235.1, 236

[56] References Cited

U.S. PATENT DOCUMENTS

| 4,709,011 | 11/1987 | Cohen et al. | 530/324 |
|---|---|---|---|
| 4,762,708 | 8/1988 | Cohen et al. | 424/89 |
| 5,149,660 | 9/1992 | Cohen et al. | 436/87 |
| 5,654,174 | 8/1997 | Cohen et al. | 435/69.3 |

OTHER PUBLICATIONS

Finberg, R & Ertt, H. (1987) Use of anti–idiotypic antibodies as inmunizing antigen, pp. 7–11, Cold Spring Harbor Laboratory Publications, Cold Spring Harbor, New York 11724.

Cai et al., "Herpes Simplex Virus Type 1 ICPO Plays a Critical Role in the De Novo Synthesis of Infectiuos Virus following Transfection of Viral DNA," *J. Virol.*, 63(11): 4579–4589 (1989).

Chiang et al. "Identification of Functional Regions of Herpes Simplex Virus Glycoprotein gD by Using Linker–Insertion Mutagenesis," *J. Virol.*, 68(4): 2529–2543 (1994).

Cohen et al. "Expression of Herpes Simplex virus Type I Glycoprotein D Deletion Mutants in Mammalian Cells," *J. Virol.*, 62(8): 1932–1940 (1988).

Fields and Knipe, Eds., *Fundamental Virology*, Chapter 16, Raven Press, New York, New York (1986).

Hill et al., "Trauma to the Skin Causes Recurrence of Herpes Simplex in the Mouse," *J. gen. Virol.*, 39: 21–28 (1978).

Hill et al., "Adrenergically induced recurrent HSV–1 corneal epithelial lesions," *Curr. Eye Res.*, 6(8): 1065–1071 (1987).

Johnson et al., "Soluble Forms of Herpes Simplex Virus Glycoprotein D Bind to a Limited Number of Cell Surface Receptors and Inhibit Virus Entry into Cells," *J. Virol.*, 64(6): 2569–2576 (Jun. 1990).

Kunkel et al., "Rapid and Efficient Site–Specific Mutagenesis without Phenotypic Selection," *Methods Enzymol.*, 154: 367–382 (1987).

Landolfi et al., "Baculovirus–expressed herpes simplex virus type 2 glycoprotein D is immunogenic and protective against lethal HSV challenge," *Vaccine*, 11: 407–414 (1993).

Ligas and Johnson, "A Herpes Simplex Virus Mutant in Which Glycoprotein D Sequences Are Replaced by β–Galactosidase Sequences Binds to but Is Unable To Penetrate into Cells," *J. Virol.*, 62(5): 1486–1494 (1988).

Long et al., "Glycoprotein D Protects Mice Against Lethal Challenge with Herpes Simplex Virus Types 1 and 2," *Infect. Immun.*, 37(2): 761–764 (1984).

Martin et al., "Soluble Glycoprotein D Blocks Herpes Simplex Virus Type 1 Infection of Rat Eye," *J. Virol.*, 66(9): 5183–5189 (Sep. 1992).

Metcalf et al., "Herpetic Keratitis in Athymic (Nude) Mice," *Infect, Immun.*, 26(3): 1164–1171 (1979).

Muggeridge et al., "Identification of a Site on Herpes Simplex Virus Type I Glycoprotein D That Is Essential for Infectivity," *J. Virol.*, 64(8): 3617–3626 (1990).

*Remmington: The Science and Practice of Pharmacy*, 19th Edition, Mack Publishing Co., Easton, PA (1995).

(List continued on next page.)

*Primary Examiner*—Michael P. Woodward
*Assistant Examiner*—Rebecca A. Fuldner
*Attorney, Agent, or Firm*—Marshall, O'Toole, Gerstein, Murray & Borun

[57] ABSTRACT

The present invention provides variant HSV-1 glycoprotein D and HSV-2 glycoprotein D molecules capable of preventing infection of cells by herpes simplex virus types 1 and/or 2. Also provided are novel purified and isolated polynucleotides encoding the variant gD molecules. HSV gD-1 and gD-2 region IV variants or fragments thereof are specifically contemplated by the invention. The presently preferred variant molecule gD-1(Δ290–299t) is the product of recombinant expression in Sf9 cells of a fusion protein including the signal peptide of honeybee melittin and Patton strain HSV-1 gD wherein (1) the Patton strain amino acid residues 290 through 299 of the mature gD-1 protein have been replaced with the amino acid residues arginine, lysine, isoleucine and phenylalanine, and (2) Patton strain amino acid residues 308 through 369 have been replaced with five histidine residues. When exposed in Sf9 cells, cleavage of the melittin signal peptide results in the presence of aspartate and proline residues at the amino terminus of the variant molecule. The amino acid sequence of gD-1(Δ290–299t) is set out in SEQ ID NO: 2 and the preferred DNA sequence encoding gD-1(Δ290–299t) is set out in SEQ ID NO: 1. Administration of gD variant molecules of the invention to mammalian subjects, especially humans, for the purpose of preventing HSV infection and/or ameliorating pathological sequelae of HSV infection is specifically contemplated.

4 Claims, 12 Drawing Sheets

OTHER PUBLICATIONS

Rock and Fraser, "Detection of HSV–1 genome in central nervous system of latently infected mice," *Nature*, 302(7): 523–525 (1983).

Sisk et al., "High–Level Expression and Purification of Secreted Forms of Herpes Simplex Virus Type 1 Glycoprotein gD Synthesized by Baculovirus–Infected Insect Cells," *J. Virol.*, 68(2): 766–775 (1994).

Stanberry et al., "Genital Herpes in Guinea Pigs: Pathogenesis of the Primary Infection and Description of Recurrent Disease," *J. Infect. Dis.*, 146(3): 397–404 (Sep. 1982).

Stanberry, L.R., "Pathogenesis of Herpes Simplex Virus Infection and Animal Models for its Study," *Current Topics in Microbiol. and Immuno.*, 179: 15–30 (1992).

Stevens, "Human Herpesviruses: a Consideration of the Latent State," *Microbiol. Rev.*, 53(3): 318–332 (1989).

Stevens and Cook, "Latent Herpes Simplex Virus in Spinal Ganglia of Mice," *Science*, 173: 843–845 (1971).

Straus et al., "Supression of Frequently Recurring Genital Herpes, A Placebo–Controlled Double–Blind Trial of Oral Acyclovir," *N. Eng. J. Med.*, 310(24): 1545–1550 (1984).

Tal–Singer et al., "Interaction of Herpes Simplex Virus Glycoprotein gC with Mammalian Cell Surface Molecules" *J. Virol.*, 69(7): 4471–4483 (1995).

Tenser, R.B., "Intracerebral Inoculation of Newborn and Adult Mice with Thymidine Kinase–Deficient Mutants of Herpes Simplex Virus Type 1," *J. Infect. Dis.*, 147: 956 (May 1983).

Tessier et al., "Enhanced secretion from insect cells of a foreign protein fused to the honeybee melittin signal peptide," *Gene*, 98: 177–183 (1991).

van Regenmortel and Neurath Eds., *Chapter 20 in Immunochemistry of Viruses, II. The Basis for Serodiagnosis and Vaccines*, Elsevier Science Publishers B. V. (1990).

Watson et al., "Herpes Simplex Virus Type–1 Glycoprotein D Gene: Nucleotide Sequence and Expression in *Escherichia coli,*" *Science*, 218(22): 381–384 (Oct. 982).

Dean et al., "Single Amino Acid Substitutions in gD of Herpes Simplex Virus 1 Confer Resistance to gD–Mediated Interference and Cause Cell–Type–Dependent Alterations in Infectivity," *Virology*, 199: 67–80 (1994).

Dean et al., "Viral Determinants of the Variable Sensitivity of Herpes Simplex Virus Strains to gD–Mediated Interference," *J. Virol.*, 69 (8): 5171–5176 (1995).

Nicola et al., "Structure Function Analysis of Soluble Forms of Herpes Simplex Virus Glycoprotein D," *J. Virol.*, 70 (6): 3815–3822 (Jun. 1996).

Full length gD gD-1(306t)

gD-1(Δ290-299t)

```
gD-1  KYALADASLKMADPNRFRGKDLPVLDQLTDPPGVRRVYHI       40
gD-2       P              N                 K gD-1  QAGLPDPFQPPSLPITVYYAVLERACRSVLLNAPSEAPQI       80
gD-2  -PS E          I                   H gD-1  VRGASEDVRKQPYNLTIAWFRMGGNCAIPITVMEYTECSY      120
gD-2        DEA  HT       Y   D              P gD-1  NKSLGACPIRTQPRWNYYDSFSAVSEDNLGFLMHAPAFET      160
gD-2       V       S gD-1  AGTYLRLVKINDWTEITQFILEHRAKGSCKYALPLRIPPS      200
gD-2                           RA           A gD-1  ACLSPQYQQGVTVDSIGMLPRFIPENQRTVAVYSLKIAG       240
gD-2      TSK                            L gD-1  WHGPKAPYTSTLLPPELSETPNATQPELAPEDPEDSALLE      280
gD-2       P           D T        V gD-1  DPVGTVAPQIPPNWHIPSIQDAATPYHPPATPNNMGLIAG      320
gD-2    A   SS          V   H A  A S P   I       319 gD-1  AVGGSLLAALVICGIVYWMHRRTKAPKRIRLPHIREDDQ      360
gD-2    LA T      G    AF VR AQM     L    D  A    359 gD-1  PSSHQPLFY                                     369
gD-2  P                                             368
```

FIGURE 2

| ASSAY | WHEN ADDED | PROTEIN | | | | | | | |
|---|---|---|---|---|---|---|---|---|---|
| | | gD-1(306t) | ∇34t | ∇126t | ∇243t | Δ290-299t | gD-2(306t) | Heat denatured gD-1(306t) | BSA |
| Plaque formation | Pre-adsorption (4°C) | 1.6 | NE | 2.4 | 4.2 | 0.004 | 0.41 | NE | NE |
| Plaque formation | Post-adsorption (4°C) | 0.45 | | | 2.1 | 0.04 | | | |
| Cell to cell spread | 3 hr post infection (37°C) | 3.6 | NE | 3.8 | >5.6 | 0.19 | >5.6 | NE | NE |
| Entry* | Pre-adsorption (4°C) | 3.7 | NE | >5.6 | 9.0 | 0.19 | >11.2 | NE | NE |

FIGURE 8

HERPES SIMPLEX VIRUS GLYCOPROTEIN D VARIANTS

FIELD OF THE INVENTION

The present invention relates generally to novel herpes simplex virus glycoprotein D molecules. More particularly, the present invention relates to variant glycoprotein D molecules which are capable of blocking infection of cells by herpes simplex virus.

BACKGROUND OF THE INVENTION

Herpes simplex viruses (HSV) are human pathogens which cause a variety of disease states including cold sores, eye and genital infections, life-threatening neonatal infections, and encephalitis. HSV is also capable of establishing latent infections in ganglia. The strains designated HSV-1 (oral) and HSV-2 (genital) are members of the family Herpesviridae and are classified in the subfamily alphaherpesvirinae and the genus simplex virus. The viruses have an enveloped double-stranded DNA genome of 150 kilobases (kb) including at least seventy-two open reading frames which encode at least eleven glycoproteins. The genomes of HSV-1 and HSV-2 exhibit extensive homology in regions which are known to encode proteins responsible for antigenic specificity and/or biological activity.

Upon infection, several viral glycoproteins act singly or in concert to bind HSV to a susceptible cell and trigger direct fusion between the virion envelope and the cell membrane. Glycoprotein D (gD) of HSV is a component of the virion envelope which plays an essential role in HSV entry into susceptible mammalian cells. The evidence to date suggests that gD binds to a cellular molecule following the initial interaction of HSV glycoproteins gC and gB with heparan sulfate proteoglycans. The interaction between gD and its receptor may stabilize the virus-cell complex prior to membrane fusion which is mediated by other essential glycoproteins such as gB, gH, and gL. See Sisk et al., *J. Virol.*, 68(3): 766–775 (1994) and Tal-Singer et al., *J. Virol.*, 69(7): 4471–4483 (1995). The nucleotide sequence of the Patton strain of HSV-1 gD (gD-1) (SEQ ID NO: 3) was first reported in Watson et al., *Science*, 218: 381–384 (1982). The strain 333 HSV-2 gD (gD-2) was described in Muggeridge et al., *J. Virol.*, 64(8): 3617–3626 (1990). The nucleotide sequence of the strain 333 gD-2 gene is set out in SEQ ID NO: 14 herein.

The HSV glycoproteins have been the subject of intense research in development of vaccines useful in preventing or treating HSV infections. See especially, U.S. Pat. Nos. 4,709,011 issued Nov. 24, 1987; 4,762,708 issued Aug. 9, 1988; and 5,149,660 issued Sep. 22, 1992; all to co-inventors herein. In addition, significant effort has been expended in the development of anti-viral agents such as nucleoside analogues and interferons. Nucleoside analogues idoxuridine, trifluridine, vidarabine and acyclovir interfere with HSV genome replication. Interferons interfere with the translation of viral proteins.

While some clinical benefit in ameliorating the sequelae of HSV infection has been achieved by treatment with nucleoside analogues and interferons, therapy with both types of compounds can involve significant side effects. See Fields and Knipe, Eds., *Fundamental Virology*, Chapter 16, Raven Press, New York, N.Y. (1986). Patients treated with acyclovir, for example, may exhibit local inflammation at sites where the drug is administered, renal dysfunction, and encephalopathic changes. Moreover, HSV mutants resistant to acyclovir have been observed and suppression of recurrences ceases when acyclovir is discontinued [Straus et al., *N. Eng. J. Med.*, 310: 1545–1550 (1984)]. Experience in the use of vidarabine has revealed neurologic toxicity. Patients treated with interferon may exhibit fever, fatigue, anorexia, weight loss, nausea and vomiting, bone marrow suppression, pain at injection sites, lymphadenopathy, and mild hair loss. Fibroblast interferon has also been reported to induce the formation of anti-interferon antibodies.

There thus exists a need in the art for additional products useful in preventing or treating HSV infection.

SUMMARY OF THE INVENTION

The present invention provides variant HSV gD molecules capable of preventing infection of cells by HSV-1 and/or HSV-2. Also provided are novel purified and isolated polynucleotides (i.e., DNA and RNA both sense and antisense strands) encoding the variant gD molecules. HSV gD-1 and gD-2 region IV variants or fragments thereof are specifically contemplated by the invention.

Generally described, variant gD-1 and gD-2 molecules of the invention are subject to variation and amino acid sequence modification in "region IV" amino acid residues comprising amino acids 277 through 310 of the native Patton strain gD-1 sequence which are conserved, for example, as residues 276 through 309 of strain 333 gD-2. Modifications preferably include deletions of one or more amino acids at region IV amino acids 290–300 of gD-1 (residues 289 through 299 of gD-2) and most preferably the deletion of, e.g., gD-1 amino acids 290–299. One or more amino acid residues not normally present in region IV may replace one or more region IV residues deleted. It is also preferred that "transmembrane" region amino acid sequences ordinarily present in native gD-1 and gD-2 proteins be deleted, for example, by deletion of carboxy terminal residues 306–369 of gD-1 (305 through 368 of gD-2). The above-noted modifications do not operate to delete any of the native potential N-linked glycosylation sites of gD-1 and gD-2 polypeptides, so that recombinant expression of the molecules in host cells capable of glycosylation will ordinarily be expected to result in formation of glycoprotein products. Variant gD-1 and gD-2 proteins and glycoproteins of the invention, when produced by recombinant methods, may include additional amino acid residues as artifacts of the expression system employed (e.g., residues remaining after signal sequence processing of fusion proteins) or as a result of modification for purposes of facilitating protein/glycoprotein isolation (e.g., a polyhistidine carboxy terminal sequence).

The presently preferred gD-1 variant molecule, designated gD-1(Δ290–299t), is the product of recombinant expression in Sf9 cells of a fusion protein including the signal peptide of honeybee melittin [Tessier et al., *Gene*, 98: 177–183 (1991)] and Patton strain HSV-1 gD wherein (1) the Patton strain amino acid residues 290 through 299 of the mature gD-1 protein have been replaced with the amino acid residues arginine, lysine, isoleucine and phenylalanine, and (2) Patton strain amino acid residues 308 through 369 have been replaced with five histidine residues. When expressed in Sf9 cells, cleavage of the melittin signal peptide results in the presence of aspartate and proline residues at the amino terminus of the variant molecule. The amino acid sequence of gD-1(Δ290–299t) is set out in SEQ ID NO: 2 and the preferred DNA sequence encoding gD-1(Δ290–299t) is set out in SEQ ID NO: 1.

Also provided are full-length gD variants in which step (1) above is performed, but step (2) is not. The amino acid sequence of such a variant, designated gD-1(Δ290–299) is set out in SEQ ID NO: 11 and the preferred DNA sequence encoding gD-1(Δ290–299) is set out in SEQ ID NO: 10.

Autonomously replicating recombinant constructions such as plasmid and viral DNA vectors incorporating sequences encoding variant gD molecules and especially vectors wherein DNA encoding variant gD molecules is operatively linked to an endogenous or exogenous expression control DNA sequence and a transcription terminator are also provided.

According to another aspect of the invention, procaryotic or eucaryotic host cells are stably transformed with DNA sequences of the invention in a manner allowing the desired variant gD molecule or fragment thereof to be expressed therein. Host cells expressing variant gD molecules can serve a variety of useful purposes. Such cells constitute a valuable source of immunogen for the development of antibody substances specifically immunoreactive with the gD variants. Host cells of the invention are conspicuously useful in methods for the large scale production of variant gD molecules or fragments thereof wherein the cells are grown in a suitable culture medium and the desired polypeptide products are isolated from the cells or from the medium in which the cells are grown by, for example, immunoaffinity purification or purification on nickel affinity columns.

HSV variant gD molecules may be chemically synthesized, but are preferably produced by recombinant procedures involving procaryotic or eucaryotic host cells of the invention. The use of insect (e.g., Sf9 cells) or mammalian host cells is expected to provide for such post-translational modifications (e.g., myristolation, glycosylation, truncation, lipidation and tyrosine, serine or threonine phosphorylation) as may be needed to confer optimal biological activity on recombinant expression products of the invention. Recombinant expression products of the invention may also be chemically modified, for example, modification by attachment of polyethylene glycol groups for the purpose of prolonging the half-life of the products upon intravenous administration.

Also comprehended by the present invention are antibody substances (e.g., monoclonal and polyclonal antibodies, single chain antibodies, chimeric murine variable region/human constant region antibodies, CDR-grafted antibodies and the like) and other binding proteins specific for the variant gD molecules. Anti-idiotypic antibodies specific for the variant gD molecule-specific antibody substances are also contemplated. Antibody substances of the invention are conspicuously useful in purifying or detecting variant molecules of the invention.

Administration of gD variant molecules or fragments thereof to mammalian subjects, especially humans, for the purpose of preventing HSV infection and/or ameliorating pathological sequelae of HSV infection is specifically contemplated. Various animal models for HSV infection are accepted in the art and include, but are not limited to, the rabbit and mouse eye models of herpes keratitis [Hill et al., *Curr. Eye Res.*, 6: 1065–1071 (1987) and Rock and Fraser, *Nature*, 302: 523–525 (1983)], cutaneous herpes infection of hairless (nude) mice [Metcalf et al., *Infect. Immunol.*, 26: 1164–1171 (1979)], vaginal lesions in the guinea pig and mouse [Stanberry et al., *J. Infect. Dis.*, 146: 397–404 (1982)], foot pad model in mice [Stevens and Cook, *Science*, 173: 843–845 (1971)], zosterform skin model in mice [Hill et al., *J. Gen. Virol.*, 39: 21–28 (1982)], and experimental herpes simplex encephalitis induced by intracerebral viral inoculation in mice [Tenser, *J. Infect. Dis.*, 147: 956 (1983)]. For review, see Stevens, *Microbiol. Rev.*, 53: 318–332 (1989) and Stanberry, *Current Topics in Microbiol. and Immunol.*, 179: 15–30 (1992). The gD variant molecules are administered to the mammal in an amount sufficient to block infection of susceptible cells by HSV. Administration may be by intravenous, intramuscular, subcutaneous, oral, suppository, mucosal, or topical routes. Also contemplated is DNA immunization wherein DNA encoding a gD variant molecule of the invention is provided to a mammal.

Compositions of the invention, when administered intravenously, intramuscularly, or orally, are administered in quantities so that variant gD molecules are provided at unit doses effective at inhibiting viral infectivity, for example, unit doses of from 0.01 micrograms to 100 milligrams of gD variant molecule per kilogram of the recipient mammal's body weight. If administered orally or topically, compositions of the invention will include from about 0.0001% to 20% variant gD molecule. Compositions of the invention also include therapeutically acceptable carriers (e.g., diluents and/or adjuvants). For general dosage and formulation considerations see *Remington: The Science and Practice of Pharmacy*, 19th ed., Mack Publishing Co., Easton, Pa. (1995).

It is also contemplated that the HSV gD variant molecules may act as immunogens in a mammalian recipient when administered by systemic or mucosal routes. Immunization of animals with wild type gD stimulates the production of virus neutralizing antibodies and protects them from lethal challenge with HSV-1 and HSV-2 [Long et al., *Infect. Immunol.*, 37: 761–764 (1984)]. The contemplated dual nature of the gD variant molecules is an advantage of the invention not shared by prior anti-HSV compounds discussed herein.

BRIEF DESCRIPTION OF THE DRAWINGS

Numerous other aspects and advantages of the present invention will be apparent to those skilled in the art upon consideration of the following detailed description of illustrative embodiments thereof, reference being made to the drawing wherein:

FIG. 2 is an alignment of wild type HSV gD-1 (SEQ ID NO: 4) and gD-2 (SEQ ID NO: 15) amino acid sequences;

FIG. 8 is a table summarizing the results of the plaque formation, cell to cell spread, and HSV entry assays of the invention for region IV variant gD-1 molecules of the invention;

DETAILED DESCRIPTION OF THE INVENTION

Figure 1A:
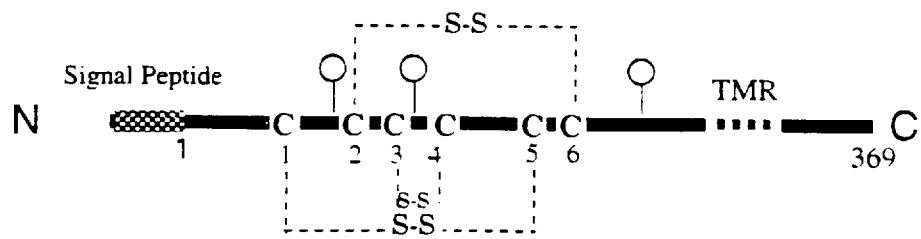
FIGS. 1A to 1C are schematic drawings of significant regions of full length wild type HSV gD-1, a carboxy terminal truncated wild type HSV gD-1 designated gD-1 (306t), and a region IV variant HSV gD-1 of the invention designated gD-1(Δ290–299t)
Figure 1B:
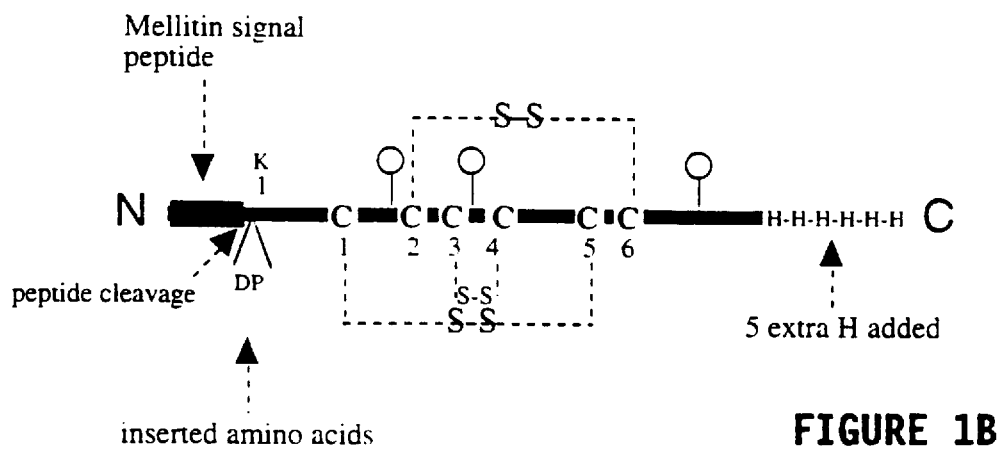
Figure 1C:
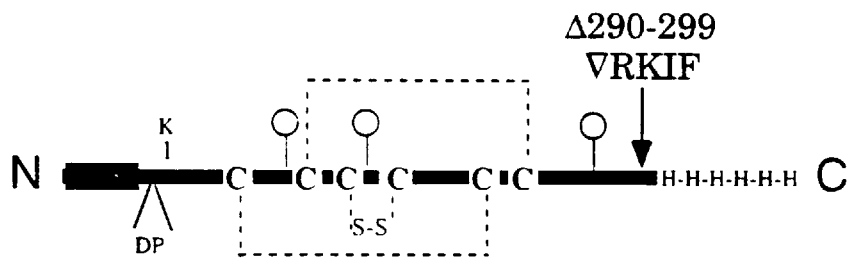
Figures 3A, 3B, 3C:
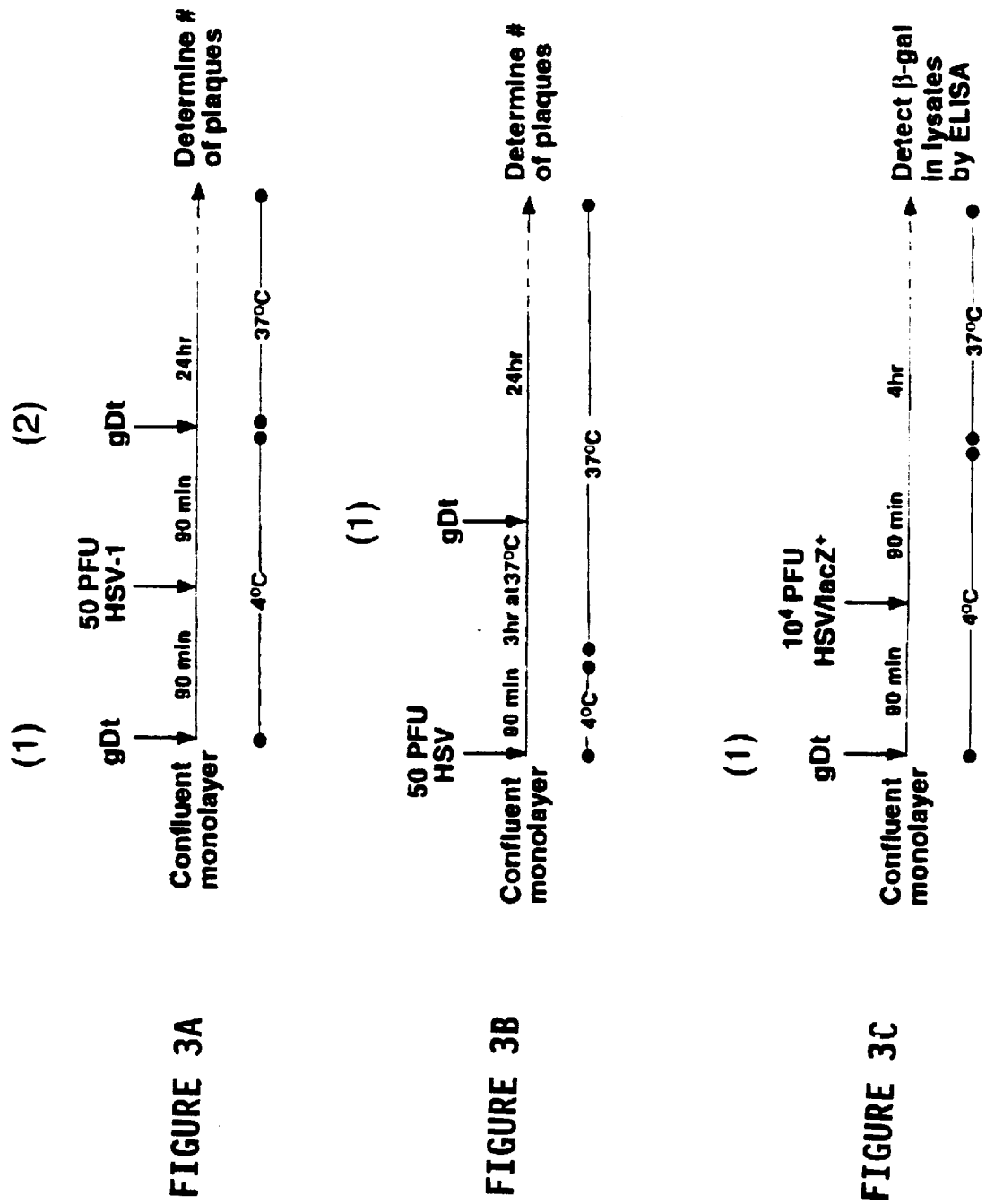
FIGS. 3A to 3C are schematic drawings of the steps in plaque formation (FIG. 3A), cell to cell spread (FIG. 3B) and virus blocking, HSV-1/lacZ+entry (FIG. 3C) assays utilized in the examples.
Figures 4A, 4B:
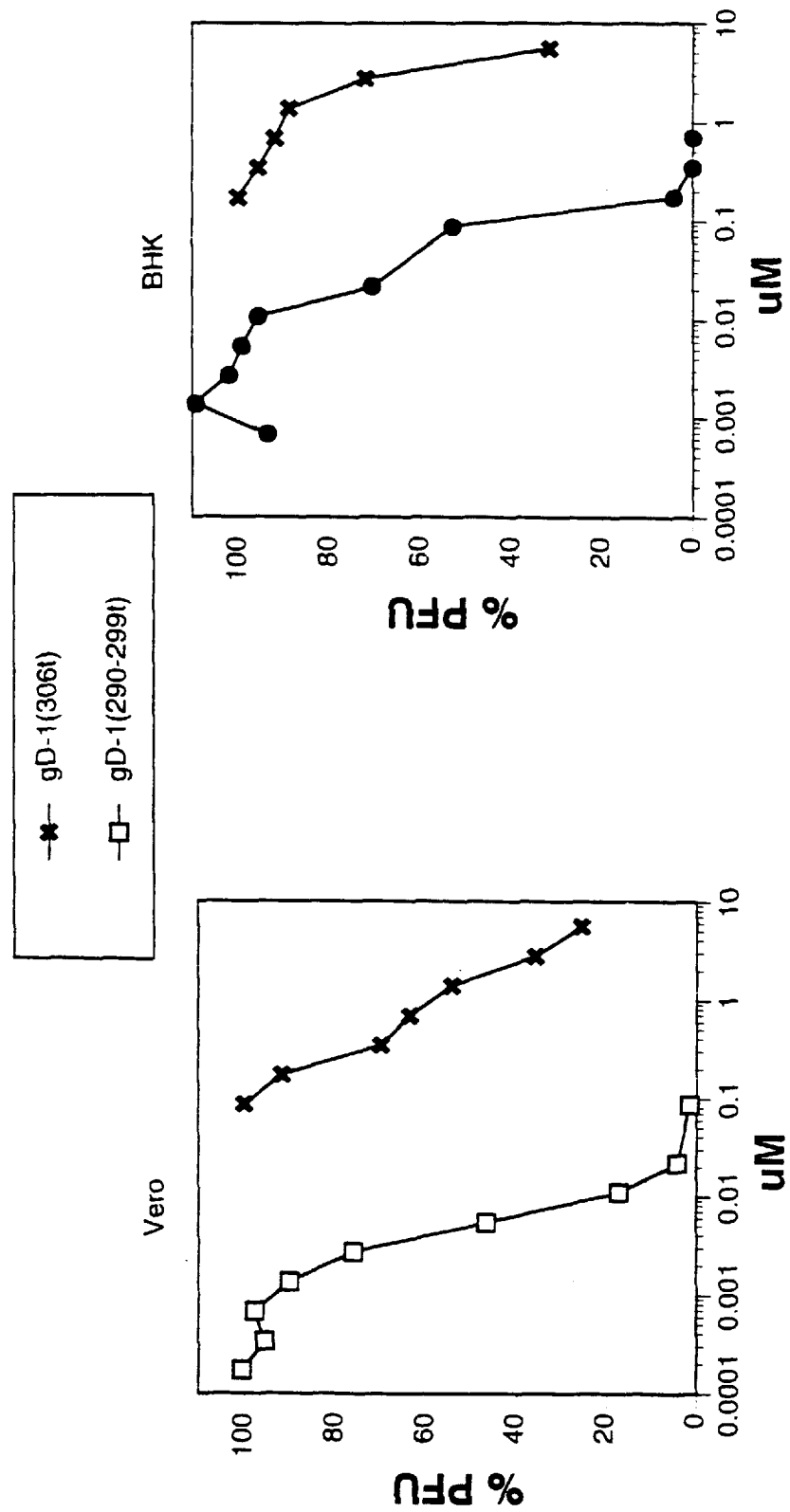
FIGS. 4A to 4B are graphs depicting the inhibitory effect of gD-1(Δ290–299t) on plaque formation on Vero (FIG. 4A) and BHK (FIG. 4B) cells exposed to HSV.
Figure 5:
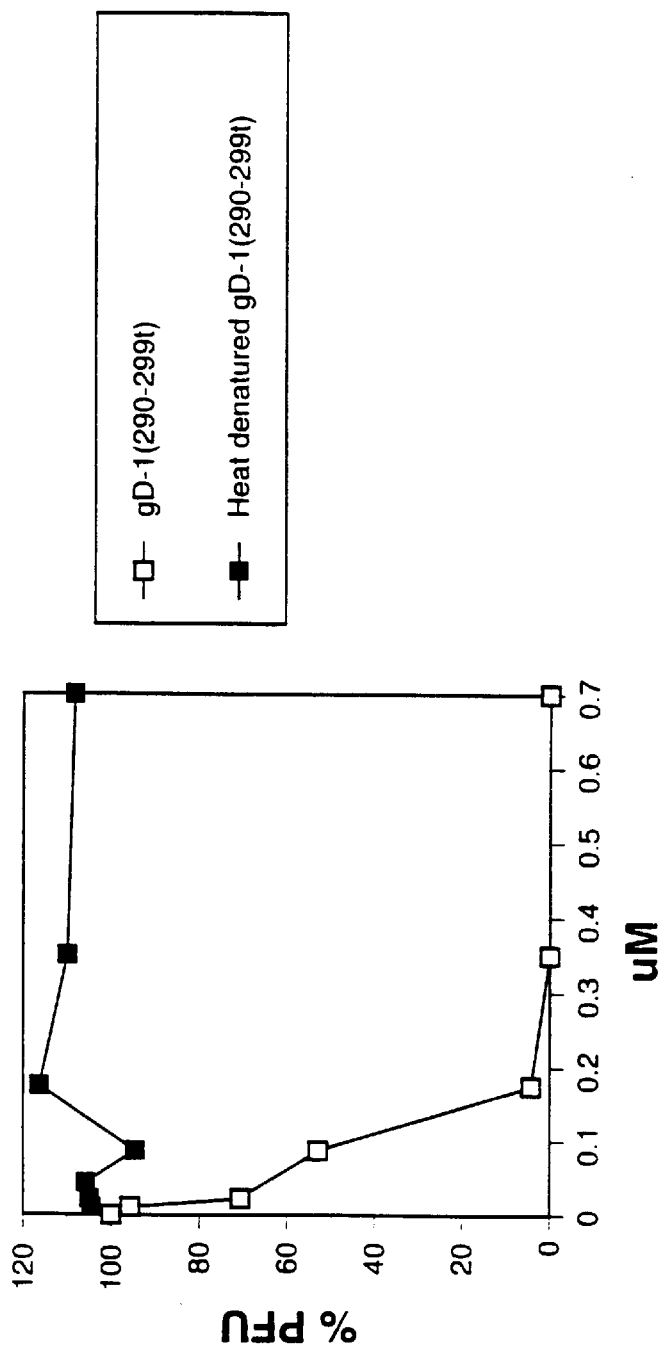
FIG. 5 is a graph depicting the effect of heat denaturation on the ability of gD-1(Δ290–299t) to block plaque formation on BHK cells exposed to HSV.
Figure 6:
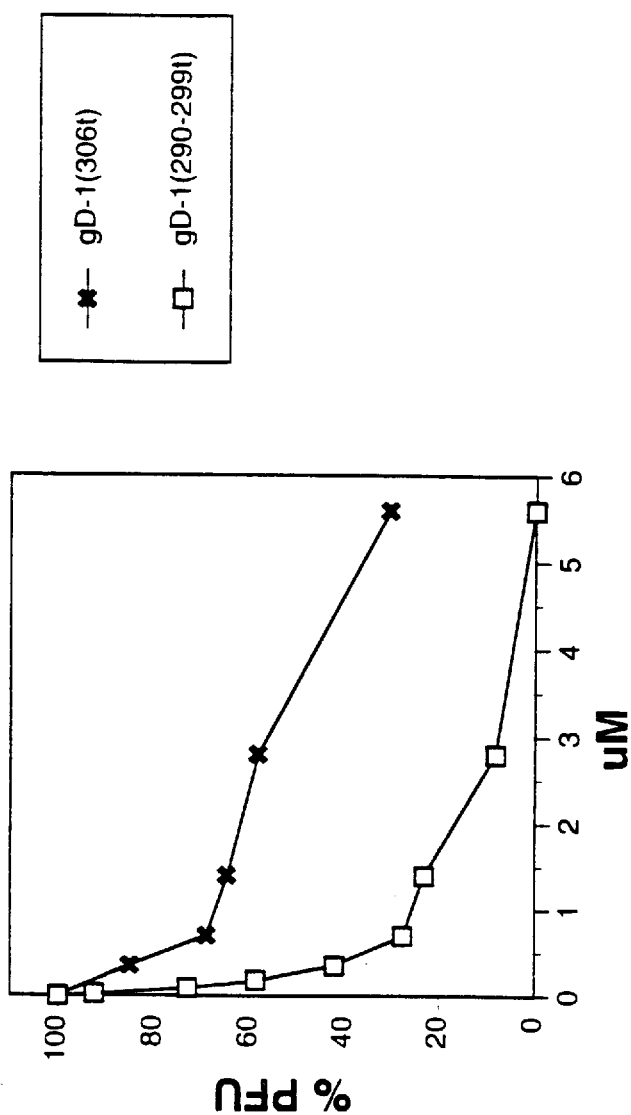
FIG. 6 is a graph illustrating the inhibitory effect of gD-1(Δ290–299t) on cell to cell spread of HSV in Vero cells.
Figure 7:
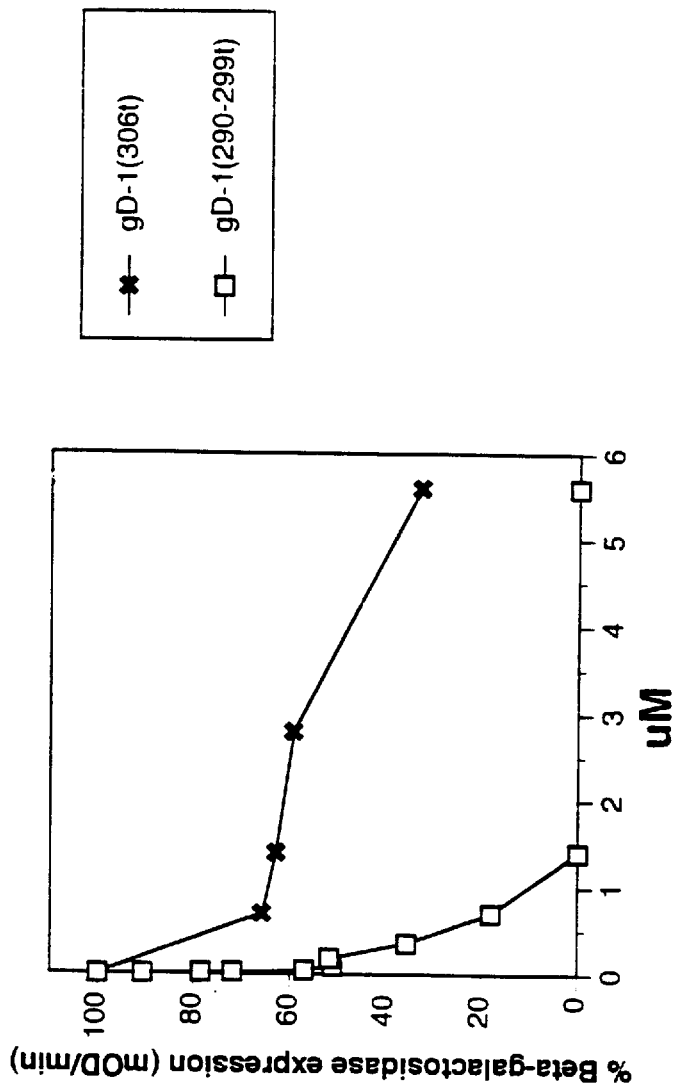
FIG. 7 is a graph depicting the inhibitory effect of gD-1(Δ290–299t) on entry of HSV into Vero cells.
Figures 9A, 9B:
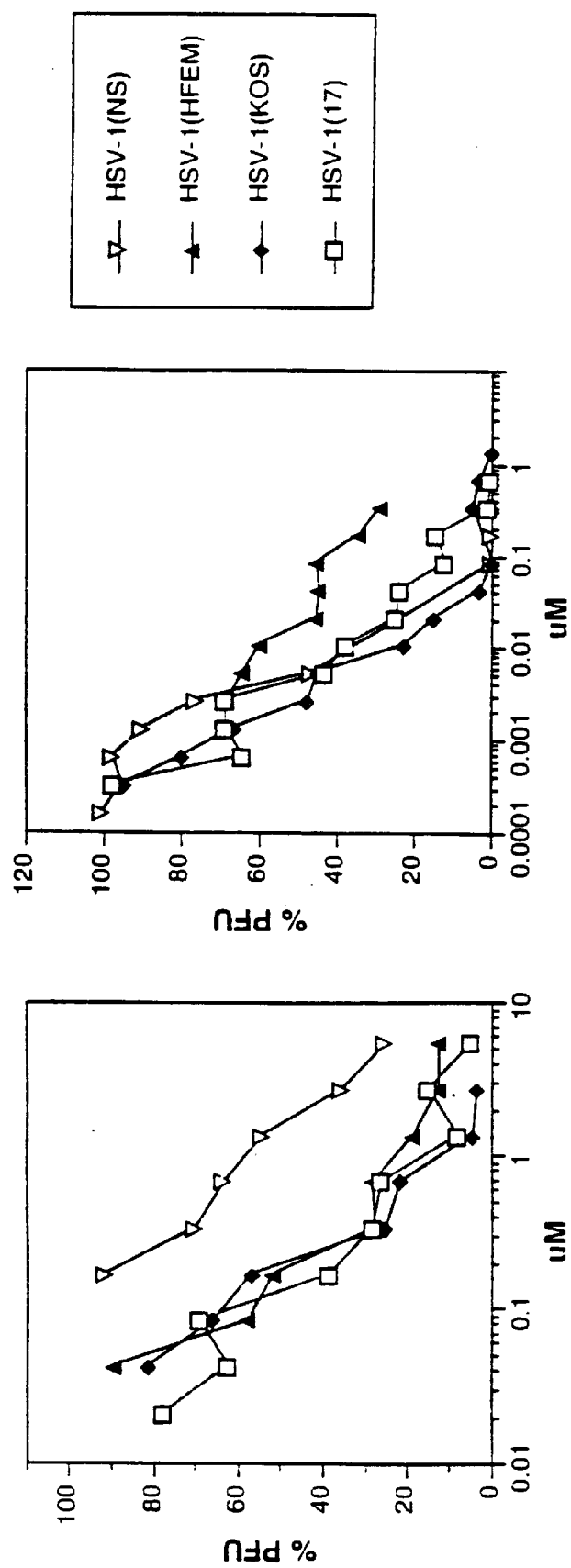
FIGS. 9A and 9B are graphs respectively showing the results of plaque formation assays in which wild type gD-1(306t) and variant gD-1(Δ290–299t) exhibited inhibitory effects on various HSV-1 strains.
Figure 10:
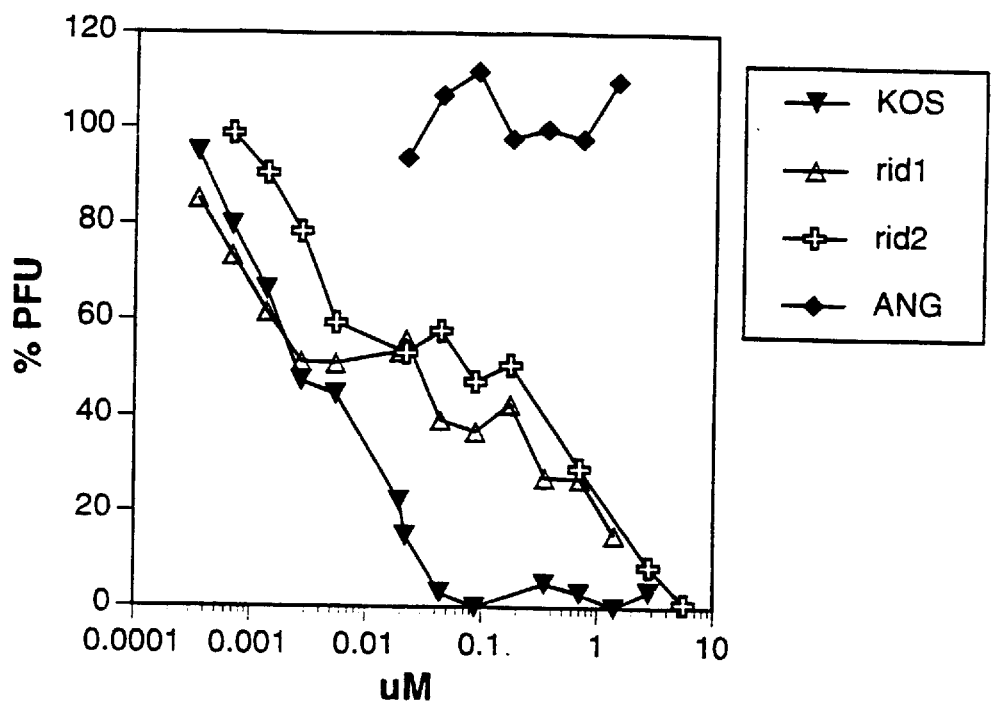
FIG. 10 is a graph depicting the effect of variant gD-1 (Δ290–299t) on the infectivity of HSV viruses resistant to inhibition by wild type gD-1 protein.

Numerous variant HSV-1 molecules were constructed and analyzed for the ability to rescue infectivity of the gD-null virus F-gDβ [Ligas and Johnson, *J. Virol.*, 62: 1486–1494 (1988)]. Variant molecules with mutations in one of four regions of gD (region I comprising amino acid residues 27 through 43, region II comprising amino acid residues 126 through 161, region III comprising amino acid residues 225 through 246, and region IV comprising amino acid residues 277 through 310) were unable to effect rescue. The four regions of gD-1 were thus determined to be necessary for entry of HSV into susceptible cells. Further analysis of representative variant molecules, each including mutations in one of the regions, identified a region IV gD variant molecule with particularly potent anti-viral activity.

The following examples illustrate the invention wherein Example 1 describes the construction of vectors encoding variant gD-1 molecules of the invention, Example 2 describes recombinant expression of the variants in mammalian and insect cells, Example 3 presents results of analyses of the conformation of the variants and the ability of the variants to complement the null virus F-gDβ, and Example 4 presents results of analyses of the ability of the variants to bind HSV susceptible cells and to block infection of HSV-susceptible cells by HSV-1 strains. Example 5 describes assays demonstrating the ability of variants of the invention to block infection by various other HSV-1 strains while Example 6 describes assays demonstrating that variants block infection of susceptible cells by HSV-2. Example 7 demonstrates the ability of variants of the invention to induce production of HSV neutralizing antibodies when the variants are utilized as immunogens. Example 8 describes methods for producing monoclonal antibodies specifically immunoreactive with variants of the invention.

EXAMPLE 1

HSV gD-1 variants were constructed by linker-insertion mutagenesis essentially as described in Chiang et al., *J. Virol.*, 68(4): 2529–2543 (1994) which is incorporated by reference herein.

A gene encoding the region IV HSV gD-1 variant gD-1 (Δ290–299t) was constructed from the wild-type gD-1 gene as follows.

First, a plasmid pHC236 containing a 12-base BglII linker inserted at amino acid 290 of gD-1, was generated by oligonucleotide-directed mutagenesis [Kunkel et al., *Methods Enzymol.*, 154: 367–382 (1988)]. The HindIII fragment containing the entire coding region of gD-1 was excised from plasmid pWW78 described in Muggeridge et al., supra, and then subcloned into the HindIII site of M13 mp18. The sequence of the Patton strain wild type gD-1 coding region present in the HindIII fragment is set out in SEQ ID NO: 3. A 37 base mutagenic oligonucleotide primer,
5' AGTTTGGTGGGAGGAAGATCTTC-CTTTGCGGCGCCAC 3'(SEQ ID NO: 5) which corresponds to nucleotides 1171 to 1196 of SEQ ID NO: 3 and which contained a 12 bp BglII linker (underlined), was used to synthesize the replicative form (RF) of M13 mp18. The mutated gD-1 gene was then excised from RF DNA and inserted into the expression vector pRSVnt EPA (Chiang et al., supra) which contains the long terminal repeat of Rous sarcoma virus as a promoter and the SV40 early polyadenylation signal. The resulting construct designated pH236 encodes full-length gD-1 with the amino acid arginine replacing isoleucine at residue 290 and the amino acids lysine, isoleucine, phenylalanine, and leucine inserted after the arginine residue.

Second, a plasmid pHC237 containing a 12-base BglII linker inserted at amino acid 300 of gD-1 was constructed by a three-step PCR procedure. The 5' segment of the gD-1 gene was synthesized using a gD-1 upstream primer,
5' CCCAAGCTTATCCTTAAGGTCTCTTT 3'(SEQ ID NO: 6) which corresponds to nucleotides 206 to 223 of SEQ ID NO: 3 and which contains the recognition sequence for the restriction enzyme HindIII (underlined) to facilitate subsequent insertion into expression vector pRSVnt EPA, and an anti-sense strand primer,
5' TCGCGGCGTCCTGGAAGATCTTCCG-GATCGACGGGAT 3'(SEQ ID NO: 7) which corresponds to nucleotides 1201 to 1225 of SEQ ID NO: 3 and which contains the BglIII linker (underlined). The primers were used to amplify gD-1 sequences from plasmid pRE4 [Cohen et al.,*J. Virol.*, 62: 1932–1940 (1988)]. The 3' segment of the gene was synthesized using a sense primer,
5' GAAGATCTTCCGAGAACCAGCGCACCGTC 3'(SEQ ID NO: 8) which corresponds to nucleotides 991 to 1008 of SEQ ID NO: 3, and a gD-1 downstream primer,
5' CCCAAGCTTCCCGCAGACCTGACCCCC 3'(SEQ ID NO: 9) which corresponds to nucleotides 1449 to 1466 of SEQ ID NO: 3 and which contains the recognition sequence for HindIII (underlined), to amplify sequences from template plasmid pRE4. In both cases, twenty-five cycles of amplification were performed; in each cycle the template was denatured at 94° C. for 1 minute, primers were then annealed to the template at 55° C. for 2 minutes, and the bound primers were extended at 72° C. for 3 minutes. The 5' and the 3' DNA segments were purified by electroelution. The segments were linked by an additional round of amplification wherein the gD-1 upstream and downstream primers and the 5' and the 3' segments as templates. The mutant DNA product was electroeluted, HindIII digested and ligated with pRSVnt EPA. The proper orientation of the insert was determined by restriction enzyme analysis. The resulting plasmid pHC237 encodes full length gD-1 with arginine, lysine, isoleucine, and phenylalanine residues inserted after amino acid 299.

Third, the BamHI-BglII fragment of pHC236 including 5' gD coding sequences was ligated to the BglII-BamHI fragment of pHC237 including 3' gD coding sequences to generate the plasmid pHC240. This plasmid encodes the variant gD molecule gD-1(Δ290–299). The DNA and deduced amino acid sequences of gD-1(Δ290–299) are set out in SEQ ID NOs: 10 and 11, respectively.

Fourth, in a further variant of this molecule, the plasmid pHC240 was further engineered to produce the plasmid designated pAN258, which contains six histidine residues at its carboxy terminus and is soluble in an aqueous medium. Amino acid residues 300 through 306 of the wild-type gD-1 protein corresponded to amino acid residues 295–300 of the variant.

Thus, a soluble form of variant gD-1(Δ290–299) was generated by PCR using plasmid pHC240 as template. Primers 5' TTTTGGATCCCAAATATGCCTTGGCGGATG 3'(SEQ ID NO: 12), which corresponds to nucleotides 316 to 334 of SEQ ID NO: 10 and contains a BamHI restriction site (underlined), and 5' GGCGCTGCGGAATGGTAGTAGTAGTAG-TAATTGACGTCTTTT 3'(SEQ ID NO: 13), which corresponds to nucleotides 1202 to 1215 of SEQ ID NO: 10 and encodes a tyrosine residue and a six residue poly histidine tail (double underlined) and a PstI site (underlined), were used to truncate the encoded protein at amino acid 306 of SEQ ID NO: 11. Forty-five amplification cycles of 1 minute at 94° C., 30 seconds at 52° C., and 2 minutes at 75° C. were performed. The amplification products were examined on a 1% agarose gel and the desired fragment was purified from the gel. The fragment was then digested with BamHI and PstI and inserted into similarly digested plasmid pVTBac [Tessier et al., supra] for use in baculovirus expression. The plasmid pVTBac includes a melittin signal peptide and cleavage site (two residues upstream of the gD-1 mature protein initial lysine residue) to allow for secretion of the protein of interest from baculovirus-infected host cells. The resulting plasmid pAN258 encoded the region IV variant gD molecule with a carboxy-terminal truncation which was designated gD-1(Δ290–299t). The DNA and deduced amino acid sequences of the variant are set out in SEQ ID NOs: 1 and 2, respectively.

Genes encoding full length and truncated region I, II, and III HSV gD-1 variant molecules were constructed by similar standard recombinant DNA methods. The full length variants were designated gD-1(∇34), gD-1(∇126), and gD-1(∇243), respectively, and the truncated variants were designated gD-1(∇34t), gD-1(∇126t), gD-1(∇243t), gD-1 (Δ277–290t), and gD-1(Δ277–300t), respectively. The full length and truncated variants gD-1(∇34) and gD-1(∇34t) contained a glycine at position 34 instead of the valine residue at position 34 of wild type gD-1 and lysine, isoleucine, phenylalanine, and leucine residues inserted after the glycine; gD-1(∇126) and gD-1(∇126t) contained a glycine at position 126 instead of the alanine residue at position 126 of wild type gD-1 and contained lysine, isoleucine, phenylalanine and proline residues inserted after the glycine; and gD-1(∇243) and gD-1(∇243t) contained a glycine residue at position 243 and contained glycine, arginine, serine, and serine residues inserted after the glycine. The truncated variants gD-1(Δ277–290t) and gD-1 (Δ277–300t) lacked Patton residues 277 to 290 and 277 to 300, respectively; were truncated at Patton amino acid 306; and contained five additional histidine residues after at the carboxy terminus. A gene encoding a secreted version of wild type gD-1 designated gD-1(306t) containing Patton strain gD-1 residues 1 through 307 and five additional histine residues at the carboxy terminus was also constructed to provide a soluble control protein.

FIG. 1 is a schematic drawing which shows significant features of wild type gD-1 and truncated wild type gD-1 (306t) and gD-1(Δ290–299t) molecules cysteine residues (c), disulfide bonds (S—S), and potential N-linked glycosylation sites.

EXAMPLE 2

Full length variant gD molecules were expressed in COS-1 or L cells transfected with the genes described in Example 1 by a modified calcium phosphate-DNA coprecipitation method described in Cohen et al., supra. Full-length variants may also be expressed using baculovirus vectors in Sf9 cells [Landolfi et al., *Vaccine,* 11: 407–414 (1993)].

Truncated variant gD molecules were expressed in Sf9 cells. pVTbac vectors containing the genes encoding the variants were cotransfected with wild type baculovirus DNA in the form of BaculoGold (Pharmingen, San Diego, Calif.) linear DNA into Sf9 cells. Cotransfection was mediated by cationic liposomes (Lipofectin, GIBCO, Grand Island, N.Y.) according to the manufacturer's specifications. Recombinant virus stocks were prepared essentially as described in Sisk et al., supra. To express the truncated variant gD molecules, suspension cultures of Sf9 cells were infected with one of the recombinant virus stocks, cells were pelleted and the medium containing the variant gD molecules was subjected to immunoaffinity chromatography on a DL-6 (produced by hybridoma ATCC HB 8606) IgG Sepharose column as described in Sisk et al., supra to purify the variants. Variants gD-1(Δ277–290t) and gD-1(Δ277–300t), in which the epitope recognized by the DL-6 antibody was deleted, can be purified by immunoaffinity chromatography using antibodies specific for other epitopes of gD-1 such as antibodies described in Muggeridge et al., Chapter 20 in van Regenmortel and Neurath, Eds., *Immunochemistry of Viruses, II, The Basis for Serodiagnosis and Vaccines,* Elsevier Science Publishers (1990).

EXAMPLE 3

The structural and functional characteristics of the variant gD-1 molecules in comparison to wild type gD-1 were examined by various assays.

The structural integrity of the variants was assessed by measuring the ability of each variant to bind to monoclonal antibodies recognizing discontinuous gD-1 epitopes as a reflection of conformation; studying cell surface expression as a reflection of proper transport, and measuring protein aggregation as an indication of improper folding. The variants were also examined by circular dichroism.

Five monoclonal antibodies (AP7, HD1, DL11, ABD, and DL2) recognizing different gD-1 discontinuous epitopes (Chiang et al., supra and Muggeridge et al., supra) were used to examine the antigenic conformation of the variants. Cytoplasmic extracts containing full length variants were prepared from COS-1 cells at 40 hours posttransfection and assayed for antibody binding by Western blot. Baculovirus-produced truncated region I, II, III, and IV variants were assayed for antibody binding by ELISA. Binding of the antibodies to the truncated variants was similar to that seen for the full length variant molecules. In each case, the variant proteins were still bound by one or more of the monoclonal antibodies which recognize conformational epitopes indicating that the conformation of the gD variants was not grossly altered by the mutations. The region IV variant was bound by all but monoclonal antibody AP7 indicating that its conformation was the most similar to wild type gD. Given the extensive homology between wild type gD-1 and gD-2 [see FIG. 2 which presents an alignment of the Patton strain gD-1 amino acid sequence (SEQ ID NO: 4) and the strain 333 gD-2 amino acid sequence (SEQ ID NO: 15)], the invention specifically contemplates that region IV gD-2 variants which contain mutations corresponding to the gD-1 mutations described herein will have similar characteristics.

When examined by circular dichroism, the region III and IV variants [gD-1(∇243) and gD-1(Δ290–299t)] resembled gD-1(306t) in secondary structure, but the region I variant gD-1(∇34) and the region II variant gD-1(∇126) differed in secondary structure.

Finally, to examine the functional characteristics of the variant gD-1 molecules, the ability of the variants to rescue the infectivity of the gD-null virus F-gDβ was assayed. The virus replicates in and forms plaques on VD60 cells which contain an integrated gD gene under the control of its own promoter. L cells transiently transfected with genes encoding a variant were then superinfected with F-gDβ. Pseudotype particles were harvested and titered on VD60 cells. The number of plaques measure the extent to which the variant gD molecule rescued the infectivity of the null virus. When infectivity was rescued with the wild type gD gene, the yields were typically $2 \times 10^6$ PFU of progeny extracellular virus and $10^6$ PFU of intracellular virus. Virus yields from wild-type gD were considered to be 100%. The region I, II, III, and IV variant gD-1 molecules were able to complement the null virus in some cases only at very low levels and in other cases not at all.

These experiments indicated that while mutations in regions I, II, III, and IV had minor effects on the conformation of the variant gD molecules, the mutations still had profound effects on the functional characteristics of the molecules.

EXAMPLE 4

Functional properties of the baculovirus-produced truncated variant gD molecules were examined further in cell binding and HSV blocking assays.

Binding of the variants to fixed Vero and BHK cells was measured by ELISA as described in Tal-Singer et al., supra. Truncated wild type gD-1(306t) and the truncated region I, II, III, and IV variant gD-1 molecules all bound to the fixed cells.

The ability of the variants to block HSV-1 infection of susceptible cells was measured by three assays diagrammed in FIG. 3, a plaque formation assay, a cell to cell spread assay, and an HSV-1/lacZ+entry assay.

The plaque formation assays were performed as described in Tal-Singer et al., supra. Briefly Vero or BHK cell monolayers in 48-well plates were treated with region I, II, III, or IV variant or BSA diluted in 5% DMEM for 1.5 hours at 4° C. HSV-1 strain NS was added at 50 PFU per well for 1.5 hours and then treated with variant or BSA. After 24 hours at 37° C., the medium was removed and the cells were fixed and air dried. Virus titers were determined by immunoperoxidase assay and the amount of variant needed to block HSV infection was titrated. Results of the assays for the truncated wild type gD-1 molecule and the gD-1 (Δ290–299t) variant are presented in FIGS. 4A and 4B. If the amount of wild type gD-1(306t) needed to block infection by more than 60% is equal to 1, the region I variant gD-1(∇34t) failed to block infection at all, the region III variant gD-1(∇243t) blocked one-half as well as wild type, and the region II variant gD-1(∇126t) blocked as well as wild type. In comparison to these results, a significant increase in ability to block infection was exhibited by the region IV variant gD-1(Δ290–299t). It was able to block infection by HSV-1 about 400 times better than wild type gD-1.

When variant gD-1(Δ290–299t) was denatured by heating to 65° C. for five minutes and then chilled to 4° C. before the plaque formation assay was performed, the variant was incapable of blocking HSV-1 infection. Heat denaturation destroys secondary and tertiary structure of gD but leaves disulfide bonds intact. See FIG. 5.

The region IV variant gD-1(Δ290–299t) exhibited similar blocking effects in cell to cell spread and HSV/lacZ+entry assays.

The cell to cell spread assay was performed in the same manner as the plaque formation assay, except that the gD proteins were not added until three hours after cells were infected with HSV-1. Results of the assays are presented in FIG. 6.

In HSV/lacZ+assays, confluent Vero cell monolayers in 96 well culture plates were preincubated with variant diluted in DMEM (BioWhittaker, Walkersville, Md.)+5% fetal bovine serum for 90 minutes at 4° C. To each well, $1.5\times10^4$ PFU/well of 7134 virus, an HSV-1 KOS strain with both copies of ICPO gene replaced by *E. coli* lacZ gene [Cai et al., *J. Virol.,* 63: 4579–4589 (1989)], corresponding to an MOI of about 0.4, was added for 90 minutes at 4° C. After four hours incubation at 37° C. the medium was removed and the cells were lysed with 0.5% NP40. The NP40 lysates were transferred to a new 96 well plate. β-galactosidase activity was detected by adding CPRG (Boehringer Mannheim, Indianapolis, Ind.) substrate solution. Absorbance was measured at 570 nm using a Microplate Biokinetics Reader (Bio-Tek Instruments, Winooski, Vt.). Results of the assay are presented in FIG. 7.

Results of the three types of assays are summarized in FIG. 8 wherein micromolar amounts of protein necessary for 50% inhibition of 50 PFU HSV (or for 50% inhibition of $1.5\times10^4$ PFU as measured by beta-galatosidase production for "entry" values) are shown and wherein "NE" indicates the protein had no effect. It is clear that while the gD-1 variants exhibit similar conformations and cell binding properties that the region IV variant is a significantly more potent HSV inhibitory compound.

EXAMPLE 5

Baculovirus-produced region IV variant gD molecules of the invention were also examined in plaque formation assays as described in Example 4 for the ability to block infection of susceptible cells by different HSV-1 strains as well as two mutant HSV-1 strains, the infectivity of which is not blocked by wild type gD-1(306t). The various strains can be differentiated by comparison of their nucleotide and amino acid sequences.

When the wild type gD-1(306t) and variant gD-1 molecule Δ290–299t were tested in plaque formation assays in which HSV-1 strains HFEM, KOS, and 17 were utilized, the variant gD-1(Δ290–299t) molecule exhibited an enhanced inhibitory effect on each strain in comparison to the wild type gD-1. Compare FIGS. 9A (306t) and 9B (Δ290–299t). These results are consistent with the results presented for HSV-1 strain NS in the foregoing example. Moreover, the variant gD-1(Δ290–299t) was able to inhibit infection by two mutant HSV-1 strains rid1 and rid2 (FIG. 10) while the wild type molecule could not. The rid1 and rid2 mutant strains were generated by passaging HSV-1 strain KOS on gD-expressing cells to select viruses that could overcome the ability of wild type gD-1 to inhibit infectivity of the viruses. See Dean et al., *Virology,* 199: 67–80 (1994). Neither wild type gD-1 (data not shown) nor the variant gD-1(Δ290–299t) was able to inhibit infection by the mutant HSV-1 strain ANG (FIG. 9). The ANG virus strain is described in Dean et al., *J. Virol.,* 69(8): 5171–5176 (1995) as a strain that is almost completely resistant to gD-mediated interference (i.e., the ANG virus can infect cells expressing gD).

Table 1 below sets out the concentration of gD-1 molecule necessary for 50% inhibition of 50 PFU HSV as measured in the plaque formation assays. In the Table, "NE" indicates the molecule had no effect on the infectivity of the indicated virus strain and "- - -" indicates the value cannot be calculated.

TABLE 1

| Virus | Strain | IC$_{50}$ (nM) gD-1(306t) | gD-1(Δ290–299t) | Fold difference |
|---|---|---|---|---|
| HSV-1 | NS | 1600 | 4.0 | 400 |
|  | KOS | 218 | 2.6 | 84 |
|  | 17 | 139 | 4.8 | 29 |
|  | HFEM | 180 | 16.4 | 11 |
|  | rid1 | NE | 131 | — |
|  | rid2 | NE | 150 | — |
| HSV-2 | 333 | 164 | 1.5 | 109 |

The region IV variant gD-1(Δ290–299t) can thus inhibit herpesviruses more effectively than wild type gD-2 protein and can inhibit herpesviruses that wild type gD-1(306t) cannot.

EXAMPLE 6

Figure 11:
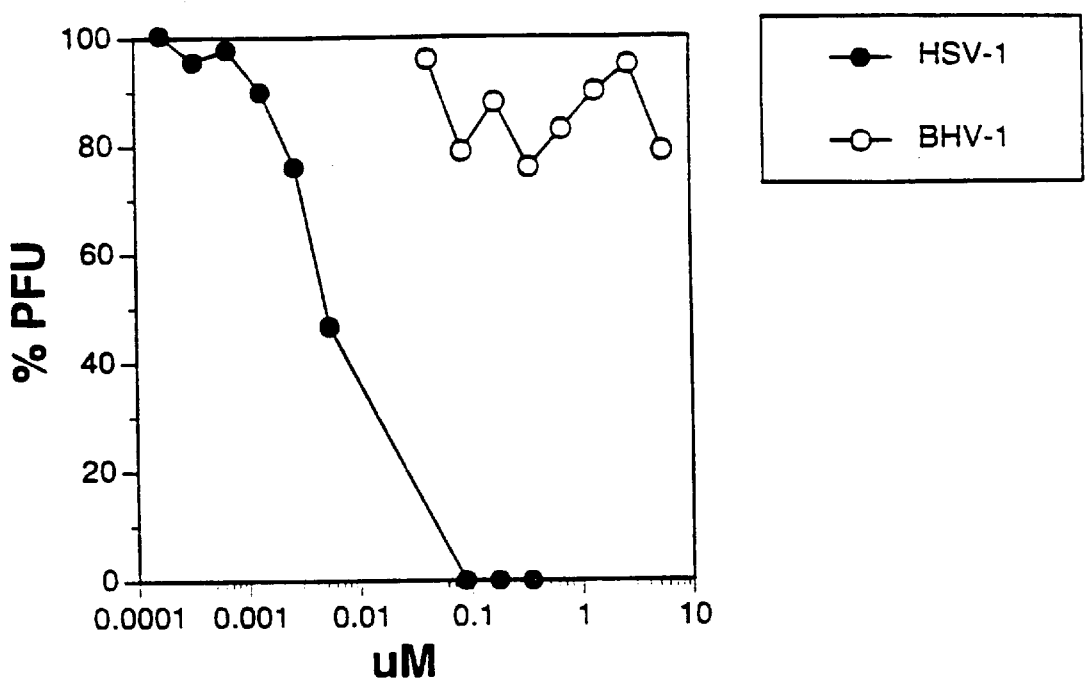
FIG. 11 is a graph showing that the inhibitory effects of variant gD-1(Δ290–299t) are specific for HSV infection.

The ability of gD-1 molecules to inhibit other herpesviruses was also investigated. The gD-1 variant (Δ290–299t) molecule was tested in plaque formation assays (Example 4) involving HSV-2 strain 333 and bovine herpes 1 (BHV-1), a related alphaherpesvirus. As shown in FIG. 11, the Δ290–299t variant inhibited HSV-1 but not BHV-1, demonstrating that its inhibitory ability is specific for HSV infection.

Figure 12:
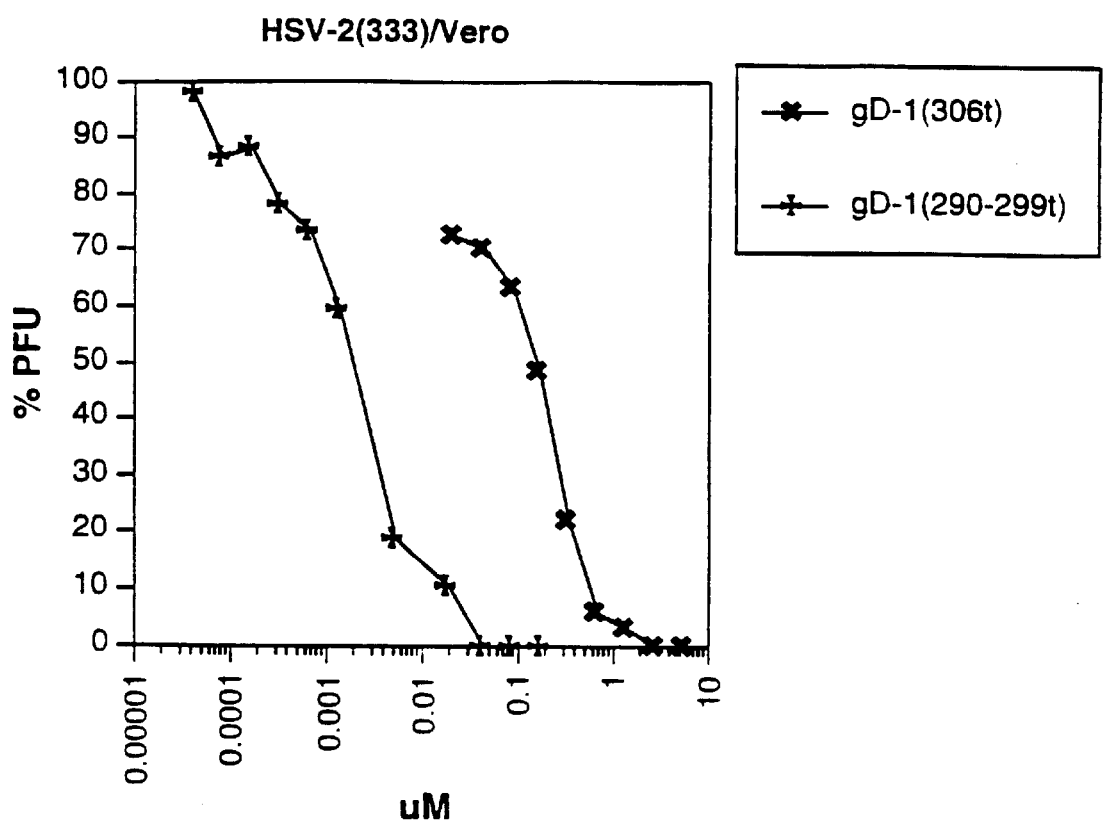
FIG. 12 is a graph revealing that variant gD-1(Δ290–299t) is more than 100 times more effective at inhibiting HSV-2 than wild type gD-1(306t).

Moreover, as shown in FIG. 12, the gD-1 variant (Δ290–299t) molecule inhibited HSV-2 at an IC$_{50}$ level of 1.5 nm while wild type gD-1 inhibited HSV-2 at an IC$_{50}$ level of 164 nm. Thus, gD-1(Δ290–299t) had a 109-fold greater effect on HSV-2 plaque formation than did wild type gD-1(306t).

EXAMPLE 7

Polyclonal antibodies specific for wild type gD-1(306t) and the gD-1 variant (Δ290–299t) molecule were elicited in rabbits. The polyclonal antbodies were then assayed for the ability to neutralize HSV-1 infectivity.

Two rabbits (designated R122 and R123) were intially immunized with an inoculation of 100 µg purified gD-1 (306t), while two rabbits (designated R130 and R131) were initially immunized with an inoculation of 100 µg purified gD-1(Δ299–299t). Both sets of initial inocula were mixed at a 1:1 ratio with Freund's complete adjuvant and given subcutaneously in inguinal and axillary regions and intramuscularly in hind limbs. No more than 0.2 ml per subcutaneous site and no more than 0.5 ml per intramuscular site were administered. After two weeks, each rabbit was boosted with 50 µg of its respective antigen mixed at a 1:1 ratio with Freund's incomplete adjuvant. The first boosts (and all subsequent boosts) were given subcutaneously along the back and intramuscularly in the hind limbs. No more than 0.2 ml per subcutaneous site and no more than 0.5 ml per intramuscular site were administered. The rabbits were similarly boosted at weeks 3, 7, 10, and 14. Tests bleeds were taken at weeks 5, 8, 11, and 16. Neutralization assays were performed with polyclonal sera from the fourth bleed.

The polyclonal antibodies were assayed for the ability to neutralize HSV-1 infectivity. The ability of the antibodies to inhibit infectivity indicates that the antigenic conformation of the variant gD molecule is similar to the wild type gD molecule. Wild type gD is known to induce production of potent virus-neutralizing antibodies when injected into animals.

The rabbit sera were heat treated at 56° C. for 30 minutes to inactivate complement. Vero cells were grown in 48 well plates until the monoplayer was nearly confluent. Serial two-fold dilutions of serum were prepared in DMEM medium containing 5% fetal bovine serum (FBS), then mixed with an equal volume of HSV-1 strain KOS in the same medium. The virus concentration was adjusted to give approximately 100 plaques per well of the 48 well plate in the absence of neutralizing antibody. Each virus-rabbit serum mixture was plated in duplicate onto the Vero cell monolayers and incubated for 1 hour at 37° C. Each well of the 48 well plate was then overlaid with medium and incubated at 37° C. until visible plaques developed. The medium was removed and the cells were fixed with a mixture of methanol and acetone and dried. Plaques were visualized by incubating the monolayers with a cocktail of antibodies to glycoproteins gD, gB and gC, then performing a "black plaque assay" using horseradish peroxidase conjugated protein A, followed by addition of the substrate 4-chloro-1-naphthol. Plaques were then counted. The results of the assays are presented in Table 2 below wherein the titer value is the dilution of antibody that reduced HSV-1 plaque number by 50%.

TABLE 2

| Polyclonal Antibody | Antigen | Neutralization titer |
|---|---|---|
| R122 | gD-1(306t) | 640 |
| R123 | gD-1(306t) | 1280 |
| R130 | gD-1(Δ290–299t) | 1280 |
| R131 | gD-1(Δ290–299t) | 640 |

Wild type and gD-1(Δ290–299t) rabbit polyclonal anitsera had similar neutralization titers suggests that gD-1 (Δ290–299t) retains wild type immunogencity. This result is consistent with the analyses of three dimensional structure presented in Example 3.

EXAMPLE 8

Monoclonal antibodies specific for gD-1 variants of the invention may be generated as follows.

To generate monoclonal antibodies, female Balb/c mice are immunized with 50 µg of a variant gD-1 molecule. The immunogen is prepared in complete Freund's adjuvant, with subsequent boosts (25 µg antigen in incomplete Freund's) at about 21 day intervals. Cell lines producing monoclonal antibodies are isolated as follows. Briefly a single cell suspension is formed by suspending immunized mouse spleen cells in serum free RPMI 1640, supplemented with 2 mM L-glutamine, 1 mM sodium pyruvate, 100 units/ml penicillin, and 100 µg/ml streptomycin (RPMI) (Gibco, Canada). The cell suspension is filtered through sterile 70-mesh Nitex cell strainer (Becton Dickinson, Parsippany, N.J.), and washed twice by centrifuging at 200 g for 5 minutes and resuspending the pellet in 20 ml serum free RPMI. Thymocytes taken from three naive Balb/c mice are prepared in this manner.

NS-1 myeloma cells kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice as described in the foregoing paragraph. After washing, each cell suspension is brought to a final volume of 10 ml in serum free RPMI, and 10 μl was diluted 10:100. Twenty μl of each dilution is removed, mixed with 20 μl 0.4% trypan blue stain in 0.85% saline (Gibco), loaded onto a hemacytometer and counted.

Two×$10^8$ spleen cells are combined with 4×$10^7$ NS-1 cells, centrifuged, and the supernatant was aspirated. The cell pellet is dislodged by tapping the tube and 2 ml of 37° C. PEG 1500 (50% in 75 mM Hepes, pH 8.0) (Boehringer Mannheim) is added with stirring over the course of 1 minute, followed by adding 14 ml of serum free RPMI over 7 minutes. An additional 16 ml RPMI is added and the cells are centrifuged at 200 g for 10 minutes. After discarding the supernatant, the pellet is resuspended in 200 ml RPMI containing 15% FBS, 100 μM sodium hypoxanthine, 0.4 μM aminopterin, 16 μM thymidine (HAT) (Gibco), 25 units/ml IL-6 (Mallinckrodt, Folcrost, Pa.), and 1.5×$10^6$ thymocytes/ml. The suspension is dispensed into ten 96-well flat bottom tissue culture plates at 200 μl/well. Cells in plates are fed 3 to 4 times between fusing and screening by aspirating approximately half the medium from each well with an 18 G needle and replenishing plating medium described above except containing 10 units/ml IL-6 and lacking thymocytes.

Fusions are screened when cell growth reaches 60–80% confluency (day 7 to 9) by ELISA on the particular gD-1 variant that was used as the immunogen in comparison to wild type gD-1 and/or other variant gD-1 molecules. Immunlon 4 plates (Dynatech, Cambridge, Mass.) are coated at 4° C. overnight with 100 ng/well protein in 30 mM carbonate buffer, pH 9.6. Plates are blocked with 100 μg/well 0.5% fish skin gelatin in PBS for one hour at 37° C., washed 3 times with PBS, 0.05% Tween 20 (PBST) and 50 μl culture supernatant is added. After incubation at 37° C. for 30 minutes, and washing as described above, 50 μl of horseradish peroxidase conjugated goat anti-mouse IgG(fc) (Jackson ImmunoResearch, West Grove, Pa.) diluted 1:3500 in PBST is added. Plates are incubated as above, washed 4 times with PBST and 100 μl substrate, consisting of 1 mg/ml o-phenyl diamine and 0.1. μl/ml $H_2O_2$ in 100 mM citrate, pH 4.5, was added. The color reaction is stopped in 5–10 minutes with the addition of 50 μl of 15% $H_2SO_4$. $A_{490}$ is read on a plate reader.

Wells showing preferential reactivity the variant preparation of interest over the control preparations are plated at limiting dilutions to isolate monoclonal cell lines producing antibodies specific for that variant gD-1 molecule.

While the present invention has been described in terms of specific embodiments, it is understood that variations and modifications will occur to those skilled in the art. For example, corresponding region IV variant gD-2 molecules and other region IV variant gD-1 molecules will be constructed and tested in the same assays for the ability to block HSV-1 and/or HSV-2 infection. Other variants specifically contemplated include, but are not limited to, variants comprising insertions at gD-1 residue 290, and variants comprising insertions at gD-1 residue 300. These variants may be made as either full-length or carboxy terminal truncated gD molecules. Accordingly only such limitations as appear in the claims should be placed on the invention.

---

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 927 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..924

( i x ) FEATURE:
        ( A ) NAME/KEY: mat_peptide
        ( B ) LOCATION: 7..924

( x i ) SEQUENCE DESCRIPTION: SEQ ID NO:1:

```
GAT  CCC  AAA  TAT  GCC  TTG  GCG  GAT  GCC  TCT  CTC  AAG  ATG  GCC  GAC  CCC        4 8
Asp  Pro  Lys  Tyr  Ala  Leu  Ala  Asp  Ala  Ser  Leu  Lys  Met  Ala  Asp  Pro
 -2         1                   5                        10

AAT  CGC  TTT  CGC  GGC  AAA  GAC  CTT  CCG  GTC  CTG  GAC  CAG  CTG  ACC  GAC        9 6
Asn  Arg  Phe  Arg  Gly  Lys  Asp  Leu  Pro  Val  Leu  Asp  Gln  Leu  Thr  Asp
 15                  20                        25                         30

CCT  CCG  GGG  GTC  CGG  CGC  GTG  TAC  CAC  ATC  CAG  GCG  GGC  CTA  CCG  GAC       1 4 4
Pro  Pro  Gly  Val  Arg  Arg  Val  Tyr  His  Ile  Gln  Ala  Gly  Leu  Pro  Asp
                        35                   40                    45

CCG  TTC  CAG  CCC  CCC  AGC  CTC  CCG  ATC  ACG  GTT  TAC  TAC  GCC  GTG  TTG       1 9 2
```

| | | | | | | | | | | | | | | | | |
|---|---|---|---|---|---|---|---|---|---|---|---|---|---|---|---|---|
|Pro|Phe|Gln|Pro|Pro|Ser|Leu|Pro|Ile|Thr|Val|Tyr|Tyr|Ala|Val|Leu| |
| | | |50| | | |55| | | | |60| | | | |

| | | | | | | | | | | | | | | | | |
|---|---|---|---|---|---|---|---|---|---|---|---|---|---|---|---|---|
|GAG|CGC|GCC|TGC|CGC|AGC|GTG|CTC|CTA|AAC|GCA|CCG|TCG|GAG|GCC|CCC|240|
|Glu|Arg|Ala|Cys|Arg|Ser|Val|Leu|Leu|Asn|Ala|Pro|Ser|Glu|Ala|Pro| |
| | |65| | | | |70| | | | |75| | | | |

| | | | | | | | | | | | | | | | | |
|---|---|---|---|---|---|---|---|---|---|---|---|---|---|---|---|---|
|CAG|ATT|GTC|CGC|GGG|GCC|TCC|GAA|GAC|GTC|CGG|AAA|CAA|CCC|TAC|AAC|288|
|Gln|Ile|Val|Arg|Gly|Ala|Ser|Glu|Asp|Val|Arg|Lys|Gln|Pro|Tyr|Asn| |
| |80| | | | |85| | | | |90| | | | | |

| | | | | | | | | | | | | | | | | |
|---|---|---|---|---|---|---|---|---|---|---|---|---|---|---|---|---|
|CTG|ACC|ATC|GCT|TGG|TTT|CGG|ATG|GGA|GGC|AAC|TGT|GCT|ATC|CCC|ATC|336|
|Leu|Thr|Ile|Ala|Trp|Phe|Arg|Met|Gly|Gly|Asn|Cys|Ala|Ile|Pro|Ile| |
|95| | | | |100| | | | |105| | | | |110| |

| | | | | | | | | | | | | | | | | |
|---|---|---|---|---|---|---|---|---|---|---|---|---|---|---|---|---|
|ACG|GTC|ATG|GAG|TAC|ACC|GAA|TGC|TCC|TAC|AAC|AAG|TCT|CTG|GGG|GCC|384|
|Thr|Val|Met|Glu|Tyr|Thr|Glu|Cys|Ser|Tyr|Asn|Lys|Ser|Leu|Gly|Ala| |
| | | | |115| | | | |120| | | | |125| | |

| | | | | | | | | | | | | | | | | |
|---|---|---|---|---|---|---|---|---|---|---|---|---|---|---|---|---|
|TGT|CCC|ATC|CGA|ACG|CAG|CCC|CGC|TGG|AAC|TAC|TAT|GAC|AGC|TTC|AGC|432|
|Cys|Pro|Ile|Arg|Thr|Gln|Pro|Arg|Trp|Asn|Tyr|Tyr|Asp|Ser|Phe|Ser| |
| | | |130| | | | |135| | | | |140| | | |

| | | | | | | | | | | | | | | | | |
|---|---|---|---|---|---|---|---|---|---|---|---|---|---|---|---|---|
|GCC|GTC|AGC|GAG|GAT|AAC|CTG|GGG|TTC|CTG|ATG|CAC|GCC|CCC|GCG|TTT|480|
|Ala|Val|Ser|Glu|Asp|Asn|Leu|Gly|Phe|Leu|Met|His|Ala|Pro|Ala|Phe| |
| | |145| | | | |150| | | | |155| | | | |

| | | | | | | | | | | | | | | | | |
|---|---|---|---|---|---|---|---|---|---|---|---|---|---|---|---|---|
|GAG|ACC|GCC|GGC|ACG|TAC|CTG|CGG|CTC|GTG|AAG|ATA|AAC|GAC|TGG|ACG|528|
|Glu|Thr|Ala|Gly|Thr|Tyr|Leu|Arg|Leu|Val|Lys|Ile|Asn|Asp|Trp|Thr| |
| |160| | | | |165| | | | |170| | | | | |

| | | | | | | | | | | | | | | | | |
|---|---|---|---|---|---|---|---|---|---|---|---|---|---|---|---|---|
|GAG|ATT|ACA|CAG|TTT|ATC|CTG|GAG|CAC|CGA|GCC|AAG|GGC|TCC|TGT|AAG|576|
|Glu|Ile|Thr|Gln|Phe|Ile|Leu|Glu|His|Arg|Ala|Lys|Gly|Ser|Cys|Lys| |
|175| | | | |180| | | | |185| | | | |190| |

| | | | | | | | | | | | | | | | | |
|---|---|---|---|---|---|---|---|---|---|---|---|---|---|---|---|---|
|TAC|GCC|CTC|CCG|CTG|CGC|ATC|CCC|CCG|TCA|GCC|TGC|CTC|TCC|CCC|CAG|624|
|Tyr|Ala|Leu|Pro|Leu|Arg|Ile|Pro|Pro|Ser|Ala|Cys|Leu|Ser|Pro|Gln| |
| | | |195| | | | |200| | | | |205| | | |

| | | | | | | | | | | | | | | | | |
|---|---|---|---|---|---|---|---|---|---|---|---|---|---|---|---|---|
|GCC|TAC|CAG|CAG|GGG|GTG|ACG|GTG|GAC|AGC|ATC|GGG|ATG|CTG|CCC|CGC|672|
|Ala|Tyr|Gln|Gln|Gly|Val|Thr|Val|Asp|Ser|Ile|Gly|Met|Leu|Pro|Arg| |
| | |210| | | | |215| | | | |220| | | | |

| | | | | | | | | | | | | | | | | |
|---|---|---|---|---|---|---|---|---|---|---|---|---|---|---|---|---|
|TTC|ATC|CCC|GAG|AAC|CAG|CGC|ACC|GTC|GCC|GTA|TAC|AGC|TTG|AAG|ATC|720|
|Phe|Ile|Pro|Glu|Asn|Gln|Arg|Thr|Val|Ala|Val|Tyr|Ser|Leu|Lys|Ile| |
| | |225| | | | |230| | | | |235| | | | |

| | | | | | | | | | | | | | | | | |
|---|---|---|---|---|---|---|---|---|---|---|---|---|---|---|---|---|
|GCC|GGG|TGG|CAC|GGG|CCC|AAG|GCC|CCA|TAC|ACG|AGC|ACC|CTG|CTG|CCC|768|
|Ala|Gly|Trp|His|Gly|Pro|Lys|Ala|Pro|Tyr|Thr|Ser|Thr|Leu|Leu|Pro| |
| |240| | | | |245| | | | |250| | | | | |

| | | | | | | | | | | | | | | | | |
|---|---|---|---|---|---|---|---|---|---|---|---|---|---|---|---|---|
|CCG|GAG|CTG|TCC|GAG|ACC|CCC|AAC|GCC|ACG|CAG|CCA|GAA|CTC|GCC|CCG|816|
|Pro|Glu|Leu|Ser|Glu|Thr|Pro|Asn|Ala|Thr|Gln|Pro|Glu|Leu|Ala|Pro| |
|255| | | | |260| | | | |265| | | | |270| |

| | | | | | | | | | | | | | | | | |
|---|---|---|---|---|---|---|---|---|---|---|---|---|---|---|---|---|
|GAA|GAC|CCC|GAG|GAT|TCG|GCC|CTC|TTG|GAG|GAC|CCC|GTG|GGG|ACG|GTG|864|
|Glu|Asp|Pro|Glu|Asp|Ser|Ala|Leu|Leu|Glu|Asp|Pro|Val|Gly|Thr|Val| |
| | | |275| | | | |280| | | | |285| | | |

| | | | | | | | | | | | | | | | | |
|---|---|---|---|---|---|---|---|---|---|---|---|---|---|---|---|---|
|GCG|CCG|CAA|AGG|AAG|ATC|TTC|CAG|GAC|GCC|GCG|ACG|CCT|TAC|CAT|CAT|912|
|Ala|Pro|Gln|Arg|Lys|Ile|Phe|Gln|Asp|Ala|Ala|Thr|Pro|Tyr|His|His| |
| | |290| | | | |295| | | | |300| | | | |

| | | | | |
|---|---|---|---|---|---|
|CAT|CAT|CAT|CAT|TAA|927|
|His|His|His|His| | |
| | |305| | | |

( 2 ) INFORMATION FOR SEQ ID NO:2:

( i ) SEQUENCE CHARACTERISTICS:
        ( A ) LENGTH: 308 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Asp  Pro  Lys  Tyr  Ala  Leu  Ala  Asp  Ala  Ser  Leu  Lys  Met  Ala  Asp  Pro

|     |     |     |     |     |     |     |     |     |     |     |     |     |     |     |
|-----|-----|-----|-----|-----|-----|-----|-----|-----|-----|-----|-----|-----|-----|-----|
| - 2 |     | 1   |     |     | 5   |     |     |     |     | 1 0 |     |     |     |     |

Asn Arg Phe Arg Gly Lys Asp Leu Pro Val Leu Asp Gln Leu Thr Asp
15                  20                  25                  30

Pro Pro Gly Val Arg Arg Val Tyr His Ile Gln Ala Gly Leu Pro Asp
            35                  40                  45

Pro Phe Gln Pro Pro Ser Leu Pro Ile Thr Val Tyr Tyr Ala Val Leu
        50                  55                  60

Glu Arg Ala Cys Arg Ser Val Leu Leu Asn Ala Pro Ser Glu Ala Pro
    65                  70                  75

Gln Ile Val Arg Gly Ala Ser Glu Asp Val Arg Lys Gln Pro Tyr Asn
        80                  85                  90

Leu Thr Ile Ala Trp Phe Arg Met Gly Gly Asn Cys Ala Ile Pro Ile
95                  100                 105                 110

Thr Val Met Glu Tyr Thr Glu Cys Ser Tyr Asn Lys Ser Leu Gly Ala
            115                 120                 125

Cys Pro Ile Arg Thr Gln Pro Arg Trp Asn Tyr Tyr Asp Ser Phe Ser
            130                 135                 140

Ala Val Ser Glu Asp Asn Leu Gly Phe Leu Met His Ala Pro Ala Phe
        145                 150                 155

Glu Thr Ala Gly Thr Tyr Leu Arg Leu Val Lys Ile Asn Asp Trp Thr
    160                 165                 170

Glu Ile Thr Gln Phe Ile Leu Glu His Arg Ala Lys Gly Ser Cys Lys
175                 180                 185                 190

Tyr Ala Leu Pro Leu Arg Ile Pro Pro Ser Ala Cys Leu Ser Pro Gln
            195                 200                 205

Ala Tyr Gln Gln Gly Val Thr Val Asp Ser Ile Gly Met Leu Pro Arg
        210                 215                 220

Phe Ile Pro Glu Asn Gln Arg Thr Val Ala Val Tyr Ser Leu Lys Ile
        225                 230                 235

Ala Gly Trp His Gly Pro Lys Ala Pro Tyr Thr Ser Thr Leu Leu Pro
    240                 245                 250

Pro Glu Leu Ser Glu Thr Pro Asn Ala Thr Gln Pro Glu Leu Ala Pro
255                 260                 265                 270

Glu Asp Pro Glu Asp Ser Ala Leu Leu Glu Asp Pro Val Gly Thr Val
            275                 280                 285

Ala Pro Gln Arg Lys Ile Phe Gln Asp Ala Ala Thr Pro Tyr His His
        290                 295                 300

His His His His
        305

(2) INFORMATION FOR SEQ ID NO:3:

(i) SEQUENCE CHARACTERISTICS:
        (A) LENGTH: 1608 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 241..1422

(ix) FEATURE:
        (A) NAME/KEY: mat_peptide
        (B) LOCATION: 316..1422

(xi) SEQUENCE DESCRIPTION: SEQ ID NO:3:

-continued

| | | | | | | | | | | |
|---|---|---|---|---|---|---|---|---|---|---|
| GTGGCCCCGG | CCCCCAACAA | AAATCACGGT | AGCCCGGCCG | TGTGACACTA | TCGTCCATAC | | | | | 60 |
| CGACCACACC | GACGAACCCC | TAAGGGGGAG | GGGCCATTTT | ACGAGGAGGA | GGGGTATAAC | | | | | 120 |
| AAAGTCTGTC | TTTAAAAAGC | AGGGGTTAGG | GAGTTGTTCG | GTCATAAGCT | TCAGCGCGAA | | | | | 180 |
| CGACCAACTA | CCCCGATCAT | CAGTTATCCT | TAAGGTCTCT | TTTGTGTGGT | GCGTTCCGGT | | | | | 240 |

```
ATG  GGG  GGG  ACT  GCC  GCC  AGG  TTG  GGG  GCC  GTG  ATT  TTG  TTT  GTC  GTC         288
Met  Gly  Gly  Thr  Ala  Ala  Arg  Leu  Gly  Ala  Val  Ile  Leu  Phe  Val  Val
-25            -20                      -15                           -10

ATA  GTG  GGC  CTC  CAT  GGG  GTC  CGC  GGC  AAA  TAT  GCC  TTG  GCG  GAT  GCC         336
Ile  Val  Gly  Leu  His  Gly  Val  Arg  Gly  Lys  Tyr  Ala  Leu  Ala  Asp  Ala
                    -5                    1                     5

TCT  CTC  AAG  ATG  GCC  GAC  CCC  AAT  CGC  TTT  CGC  GGC  AAA  GAC  CTT  CCG         384
Ser  Leu  Lys  Met  Ala  Asp  Pro  Asn  Arg  Phe  Arg  Gly  Lys  Asp  Leu  Pro
          10                      15                    20

GTC  CTG  GAC  CAG  CTG  ACC  GAC  CCT  CCG  GGG  GTC  CGG  CGC  GTG  TAC  CAC         432
Val  Leu  Asp  Gln  Leu  Thr  Asp  Pro  Pro  Gly  Val  Arg  Arg  Val  Tyr  His
     25                      30                    35

ATC  CAG  GCG  GGC  CTA  CCG  GAC  CCG  TTC  CAG  CCC  CCC  AGC  CTC  CCG  ATC         480
Ile  Gln  Ala  Gly  Leu  Pro  Asp  Pro  Phe  Gln  Pro  Pro  Ser  Leu  Pro  Ile
40                        45                    50                         55

ACG  GTT  TAC  TAC  GCC  GTG  TTG  GAG  CGC  GCC  TGC  CGC  AGC  GTG  CTC  CTA         528
Thr  Val  Tyr  Tyr  Ala  Val  Leu  Glu  Arg  Ala  Cys  Arg  Ser  Val  Leu  Leu
                         60                      65                    70

AAC  GCA  CCG  TCG  GAG  GCC  CCC  CAG  ATT  GTC  CGC  GGG  GCC  TCC  GAA  GAC         576
Asn  Ala  Pro  Ser  Glu  Ala  Pro  Gln  Ile  Val  Arg  Gly  Ala  Ser  Glu  Asp
               75                      80                    85

GTC  CGG  AAA  CAA  CCC  TAC  AAC  CTG  ACC  ATC  GCT  TGG  TTT  CGG  ATG  GGA         624
Val  Arg  Lys  Gln  Pro  Tyr  Asn  Leu  Thr  Ile  Ala  Trp  Phe  Arg  Met  Gly
          90                      95                    100

GGC  AAC  TGT  GCT  ATC  CCC  ATC  ACG  GTC  ATG  GAG  TAC  ACC  GAA  TGC  TCC         672
Gly  Asn  Cys  Ala  Ile  Pro  Ile  Thr  Val  Met  Glu  Tyr  Thr  Glu  Cys  Ser
     105                      110                    115

TAC  AAC  AAG  TCT  CTG  GGG  GCC  TGT  CCC  ATC  CGA  ACG  CAG  CCC  CGC  TGG         720
Tyr  Asn  Lys  Ser  Leu  Gly  Ala  Cys  Pro  Ile  Arg  Thr  Gln  Pro  Arg  Trp
120                      125                    130                         135

AAC  TAC  TAT  GAC  AGC  TTC  AGC  GCC  GTC  AGC  GAG  GAT  AAC  CTG  GGG  TTC         768
Asn  Tyr  Tyr  Asp  Ser  Phe  Ser  Ala  Val  Ser  Glu  Asp  Asn  Leu  Gly  Phe
               140                      145                    150

CTG  ATG  CAC  GCC  CCC  GCG  TTT  GAG  ACC  GCC  GGC  ACG  TAC  CTG  CGG  CTC         816
Leu  Met  His  Ala  Pro  Ala  Phe  Glu  Thr  Ala  Gly  Thr  Tyr  Leu  Arg  Leu
               155                      160                    165

GTG  AAG  ATA  AAC  GAC  TGG  ACG  GAG  ATT  ACA  CAG  TTT  ATC  CTG  GAG  CAC         864
Val  Lys  Ile  Asn  Asp  Trp  Thr  Glu  Ile  Thr  Gln  Phe  Ile  Leu  Glu  His
          170                      175                    180

CGA  GCC  AAG  GGC  TCC  TGT  AAG  TAC  GCC  CTC  CCG  CTG  CGC  ATC  CCC  CCG         912
Arg  Ala  Lys  Gly  Ser  Cys  Lys  Tyr  Ala  Leu  Pro  Leu  Arg  Ile  Pro  Pro
185                      190                    195

TCA  GCC  TGC  CTC  TCC  CCC  CAG  GCC  TAC  CAG  CAG  GGG  GTG  ACG  GTG  GAC         960
Ser  Ala  Cys  Leu  Ser  Pro  Gln  Ala  Tyr  Gln  Gln  Gly  Val  Thr  Val  Asp
200                      205                    210                         215

AGC  ATC  GGG  ATG  CTG  CCC  CGC  TTC  ATC  CCC  GAG  AAC  CAG  CGC  ACC  GTC        1008
Ser  Ile  Gly  Met  Leu  Pro  Arg  Phe  Ile  Pro  Glu  Asn  Gln  Arg  Thr  Val
                    220                      225                    230

GCC  GTA  TAC  AGC  TTG  AAG  ATC  GCC  GGG  TGG  CAC  GGG  CCC  AAG  GCC  CCA        1056
Ala  Val  Tyr  Ser  Leu  Lys  Ile  Ala  Gly  Trp  His  Gly  Pro  Lys  Ala  Pro
               235                      240                    245

TAC  ACG  AGC  ACC  CTG  CTG  CCC  CCG  GAG  CTG  TCC  GAG  ACC  CCC  AAC  GCC        1104
Tyr  Thr  Ser  Thr  Leu  Leu  Pro  Pro  Glu  Leu  Ser  Glu  Thr  Pro  Asn  Ala
               250                      255                    260
```

| | | | | | | | | | | | | | | | | |
|---|---|---|---|---|---|---|---|---|---|---|---|---|---|---|---|---|
| ACG | CAG | CCA | GAA | CTC | GCC | CCG | GAA | GAC | CCC | GAG | GAT | TCG | GCC | CTC | TTG | 1152 |
| Thr | Gln | Pro | Glu | Leu | Ala | Pro | Glu | Asp | Pro | Glu | Asp | Ser | Ala | Leu | Leu | |
| | | 265 | | | | 270 | | | | | 275 | | | | | |
| GAG | GAC | CCC | GTG | GGG | ACG | GTG | GCG | CCG | CAA | ATC | CCA | CCA | AAC | TGG | CAC | 1200 |
| Glu | Asp | Pro | Val | Gly | Thr | Val | Ala | Pro | Gln | Ile | Pro | Pro | Asn | Trp | His | |
| 280 | | | | | 285 | | | | | 290 | | | | | 295 | |
| ATC | CCG | TCG | ATC | CAG | GAC | GCC | GCG | ACG | CCT | TAC | CAT | CCC | CCG | GCC | ACC | 1248 |
| Ile | Pro | Ser | Ile | Gln | Asp | Ala | Ala | Thr | Pro | Tyr | His | Pro | Pro | Ala | Thr | |
| | | | | 300 | | | | | 305 | | | | | | 310 | |
| CCG | AAC | AAC | ATG | GGC | CTG | ATC | GCC | GGC | GCG | GTG | GGC | GGC | AGT | CTC | CTG | 1296 |
| Pro | Asn | Asn | Met | Gly | Leu | Ile | Ala | Gly | Ala | Val | Gly | Gly | Ser | Leu | Leu | |
| | | | 315 | | | | | 320 | | | | | 325 | | | |
| GCA | GCC | CTG | GTC | ATT | TGC | GGA | ATT | GTG | TAC | TGG | ATG | CAC | CGC | CGC | ACT | 1344 |
| Ala | Ala | Leu | Val | Ile | Cys | Gly | Ile | Val | Tyr | Trp | Met | His | Arg | Arg | Thr | |
| | | 330 | | | | | 335 | | | | | 340 | | | | |
| CGG | AAA | GCC | CCA | AAG | CGC | ATA | CGC | CTC | CCC | CAC | ATC | CGG | GAA | GAC | GAC | 1392 |
| Arg | Lys | Ala | Pro | Lys | Arg | Ile | Arg | Leu | Pro | His | Ile | Arg | Glu | Asp | Asp | |
| | 345 | | | | | 350 | | | | | 355 | | | | | |
| CAG | CCG | TCC | TCG | CAC | CAG | CCC | TTG | TTT | TAC | TAGATACCCC | CCCTTAATGG | | | | | 1442 |
| Gln | Pro | Ser | Ser | His | Gln | Pro | Leu | Phe | Tyr | | | | | | | |
| 360 | | | | | 365 | | | | | | | | | | | |

| | | | | | |
|---|---|---|---|---|---|
| GTGCGGGGGG | GTCAGGTCTG | CGGGGTTGGG | ATGGGACCTT | AACTCCATAT | AAAGCGAGTC | 1502 |
| TGGAAGGGGG | GAAAGGCGGA | CAGTCGATAA | GTCGGTAGCG | GGGGACGCGC | ACCTGTTCCG | 1562 |
| CCTGTCGCAC | CCACAGCTTT | TTCGCGAACC | GTCCCGTTTT | CGGGAT | | 1608 |

( 2 ) INFORMATION FOR SEQ ID NO:4:

( i ) SEQUENCE CHARACTERISTICS:
  ( A ) LENGTH: 394 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Gly | Gly | Thr | Ala | Ala | Arg | Leu | Gly | Ala | Val | Ile | Leu | Phe | Val | Val |
| -25 | | | | | -20 | | | | | -15 | | | | | -10 |
| Ile | Val | Gly | Leu | His | Gly | Val | Arg | Gly | Lys | Tyr | Ala | Leu | Ala | Asp | Ala |
| | | | | -5 | | | | | 1 | | | | 5 | | |
| Ser | Leu | Lys | Met | Ala | Asp | Pro | Asn | Arg | Phe | Arg | Gly | Lys | Asp | Leu | Pro |
| | | 10 | | | | | 15 | | | | | 20 | | | |
| Val | Leu | Asp | Gln | Leu | Thr | Asp | Pro | Pro | Gly | Val | Arg | Arg | Val | Tyr | His |
| | 25 | | | | | 30 | | | | | 35 | | | | |
| Ile | Gln | Ala | Gly | Leu | Pro | Asp | Pro | Phe | Gln | Pro | Pro | Ser | Leu | Pro | Ile |
| 40 | | | | | 45 | | | | | 50 | | | | | 55 |
| Thr | Val | Tyr | Tyr | Ala | Val | Leu | Glu | Arg | Ala | Cys | Arg | Ser | Val | Leu | Leu |
| | | | | 60 | | | | | 65 | | | | | 70 | |
| Asn | Ala | Pro | Ser | Glu | Ala | Pro | Gln | Ile | Val | Arg | Gly | Ala | Ser | Glu | Asp |
| | | | 75 | | | | | 80 | | | | | 85 | | |
| Val | Arg | Lys | Gln | Pro | Tyr | Asn | Leu | Thr | Ile | Ala | Trp | Phe | Arg | Met | Gly |
| | | 90 | | | | | 95 | | | | | 100 | | | |
| Gly | Asn | Cys | Ala | Ile | Pro | Ile | Thr | Val | Met | Glu | Tyr | Thr | Glu | Cys | Ser |
| | 105 | | | | | 110 | | | | | 115 | | | | |
| Tyr | Asn | Lys | Ser | Leu | Gly | Ala | Cys | Pro | Ile | Arg | Thr | Gln | Pro | Arg | Trp |
| 120 | | | | | 125 | | | | | 130 | | | | | 135 |
| Asn | Tyr | Tyr | Asp | Ser | Phe | Ser | Ala | Val | Ser | Glu | Asp | Asn | Leu | Gly | Phe |
| | | | | 140 | | | | | 145 | | | | | 150 | |
| Leu | Met | His | Ala | Pro | Ala | Phe | Glu | Thr | Ala | Gly | Thr | Tyr | Leu | Arg | Leu |

```
                          155                          160                            165
Val  Lys  Ile  Asn  Asp  Trp  Thr  Glu  Ile  Thr  Gln  Phe  Ile  Leu  Glu  His
          170                      175                      180

Arg  Ala  Lys  Gly  Ser  Cys  Lys  Tyr  Ala  Leu  Pro  Leu  Arg  Ile  Pro  Pro
          185                      190                      195

Ser  Ala  Cys  Leu  Ser  Pro  Gln  Ala  Tyr  Gln  Gln  Gly  Val  Thr  Val  Asp
200                           205                 210                     215

Ser  Ile  Gly  Met  Leu  Pro  Arg  Phe  Ile  Pro  Glu  Asn  Gln  Arg  Thr  Val
                    220                      225                      230

Ala  Val  Tyr  Ser  Leu  Lys  Ile  Ala  Gly  Trp  His  Gly  Pro  Lys  Ala  Pro
               235                      240                      245

Tyr  Thr  Ser  Thr  Leu  Leu  Pro  Pro  Glu  Leu  Ser  Glu  Thr  Pro  Asn  Ala
          250                      255                      260

Thr  Gln  Pro  Glu  Leu  Ala  Pro  Glu  Asp  Pro  Glu  Asp  Ser  Ala  Leu  Leu
     265                           270                 275

Glu  Asp  Pro  Val  Gly  Thr  Val  Ala  Pro  Gln  Ile  Pro  Pro  Asn  Trp  His
280                      285                      290                           295

Ile  Pro  Ser  Ile  Gln  Asp  Ala  Ala  Thr  Pro  Tyr  His  Pro  Pro  Ala  Thr
                    300                      305                      310

Pro  Asn  Asn  Met  Gly  Leu  Ile  Ala  Gly  Ala  Val  Gly  Gly  Ser  Leu  Leu
                    315                      320                      325

Ala  Ala  Leu  Val  Ile  Cys  Gly  Ile  Val  Tyr  Trp  Met  His  Arg  Arg  Thr
               330                      335                      340

Arg  Lys  Ala  Pro  Lys  Arg  Ile  Arg  Leu  Pro  His  Ile  Arg  Glu  Asp  Asp
          345                      350                      355

Gln  Pro  Ser  Ser  His  Gln  Pro  Leu  Phe  Tyr
360                      365
```

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

AGTTTGGTGG GAGGAAGATC TTCCTTTGCG GCGCCAC                                    37

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CCCAAGCTTA TCCTTAAGGT CTCTTT                                                26

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear (i i) MOLECULE TYPE: DNA (x i) SEQUENCE DESCRIPTION: SEQ ID NO:7:

```
TCGCGGCGTC CTGGAAGATC TTCCGGATCG ACGGGAT                                    37
```

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:8:

```
GAAGATCTTC CGAGAACCAG CGCACCGTC                                             29
```

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:9:

```
CCCAAGCTTC CCGCAGACCT GACCCCC                                               27
```

(2) INFORMATION FOR SEQ ID NO:10:

(i) SEQUENCE CHARACTERISTICS:
        (A) LENGTH: 1550 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 241..1404

(i x) FEATURE:
        (A) NAME/KEY: mat_peptide
        (B) LOCATION: 316..1404

(x i) SEQUENCE DESCRIPTION: SEQ ID NO:10:

```
GTGGCCCCGG CCCCCAACAA AAATCACGGT AGCCCGGCCG TGTGACACTA TCGTCCATAC           60
CGACCACACC GACGAACCCC TAAGGGGGAG GGGCCATTTT ACGAGGAGGA GGGGTATAAC          120
AAAGTCTGTC TTTAAAAAGC AGGGGTTAGG GAGTTGTTCG GTCATAAGCT TCAGCGCGAA          180
CGACCAACTA CCCCGATCAT CAGTTATCCT TAAGGTCTCT TTTGTGTGGT GCGTTCCGGT          240

ATG GGG GGG ACT GCC GCC AGG TTG GGG GCC GTG ATT TTG TTT GTC GTC            288
Met Gly Gly Thr Ala Ala Arg Leu Gly Ala Val Ile Leu Phe Val Val
-25                 -20                 -15                 -10

ATA GTG GGC CTC CAT GGG GTC CGC GGC AAA TAT GCC TTG GCG GAT GCC            336
Ile Val Gly Leu His Gly Val Arg Gly Lys Tyr Ala Leu Ala Asp Ala
            -5                  1                   5

TCT CTC AAG ATG GCC GAC CCC AAT CGC TTT CGC GGC AAA GAC CTT CCG            384
Ser Leu Lys Met Ala Asp Pro Asn Arg Phe Arg Gly Lys Asp Leu Pro
        10                  15                  20

GTC CTG GAC CAG CTG ACC GAC CCT CCG GGG GTC CGG CGC GTG TAC CAC            432
Val Leu Asp Gln Leu Thr Asp Pro Pro Gly Val Arg Arg Val Tyr His
        25                  30                  35
```

| | | | | | | | | | | | | | | | | |
|---|---|---|---|---|---|---|---|---|---|---|---|---|---|---|---|---|
| ATC | CAG | GCG | GGC | CTA | CCG | GAC | CCG | TTC | CAG | CCC | CCC | AGC | CTC | CCG | ATC | 480 |
| Ile | Gln | Ala | Gly | Leu | Pro | Asp | Pro | Phe | Gln | Pro | Pro | Ser | Leu | Pro | Ile | |
| 40 | | | | 45 | | | | | 50 | | | | | | 55 | |
| ACG | GTT | TAC | TAC | GCC | GTG | TTG | GAG | CGC | GCC | TGC | CGC | AGC | GTG | CTC | CTA | 528 |
| Thr | Val | Tyr | Tyr | Ala | Val | Leu | Glu | Arg | Ala | Cys | Arg | Ser | Val | Leu | Leu | |
| | | | | 60 | | | | 65 | | | | | | 70 | | |
| AAC | GCA | CCG | TCG | GAG | GCC | CCC | CAG | ATT | GTC | CGC | GGG | GCC | TCC | GAA | GAC | 576 |
| Asn | Ala | Pro | Ser | Glu | Ala | Pro | Gln | Ile | Val | Arg | Gly | Ala | Ser | Glu | Asp | |
| | | | 75 | | | | | 80 | | | | | 85 | | | |
| GTC | CGG | AAA | CAA | CCC | TAC | AAC | CTG | ACC | ATC | GCT | TGG | TTT | CGG | ATG | GGA | 624 |
| Val | Arg | Lys | Gln | Pro | Tyr | Asn | Leu | Thr | Ile | Ala | Trp | Phe | Arg | Met | Gly | |
| | | 90 | | | | | 95 | | | | | 100 | | | | |
| GGC | AAC | TGT | GCT | ATC | CCC | ATC | ACG | GTC | ATG | GAG | TAC | ACC | GAA | TGC | TCC | 672 |
| Gly | Asn | Cys | Ala | Ile | Pro | Ile | Thr | Val | Met | Glu | Tyr | Thr | Glu | Cys | Ser | |
| | 105 | | | | | 110 | | | | | 115 | | | | | |
| TAC | AAC | AAG | TCT | CTG | GGG | GCC | TGT | CCC | ATC | CGA | ACG | CAG | CCC | CGC | TGG | 720 |
| Tyr | Asn | Lys | Ser | Leu | Gly | Ala | Cys | Pro | Ile | Arg | Thr | Gln | Pro | Arg | Trp | |
| 120 | | | | | 125 | | | | | 130 | | | | | 135 | |
| AAC | TAC | TAT | GAC | AGC | TTC | AGC | GCC | GTC | AGC | GAG | GAT | AAC | CTG | GGG | TTC | 768 |
| Asn | Tyr | Tyr | Asp | Ser | Phe | Ser | Ala | Val | Ser | Glu | Asp | Asn | Leu | Gly | Phe | |
| | | | | 140 | | | | | 145 | | | | | | 150 | |
| CTG | ATG | CAC | GCC | CCC | GCG | TTT | GAG | ACC | GCC | GGC | ACG | TAC | CTG | CGG | CTC | 816 |
| Leu | Met | His | Ala | Pro | Ala | Phe | Glu | Thr | Ala | Gly | Thr | Tyr | Leu | Arg | Leu | |
| | | | 155 | | | | | 160 | | | | | 165 | | | |
| GTG | AAG | ATA | AAC | GAC | TGG | ACG | GAG | ATT | ACA | CAG | TTT | ATC | CTG | GAG | CAC | 864 |
| Val | Lys | Ile | Asn | Asp | Trp | Thr | Glu | Ile | Thr | Gln | Phe | Ile | Leu | Glu | His | |
| | | 170 | | | | | 175 | | | | | 180 | | | | |
| CGA | GCC | AAG | GGC | TCC | TGT | AAG | TAC | GCC | CTC | CCG | CTG | CGC | ATC | CCC | CCG | 912 |
| Arg | Ala | Lys | Gly | Ser | Cys | Lys | Tyr | Ala | Leu | Pro | Leu | Arg | Ile | Pro | Pro | |
| | 185 | | | | | 190 | | | | | 195 | | | | | |
| TCA | GCC | TGC | CTC | TCC | CCC | CAG | GCC | TAC | CAG | CAG | GGG | GTG | ACG | GTG | GAC | 960 |
| Ser | Ala | Cys | Leu | Ser | Pro | Gln | Ala | Tyr | Gln | Gln | Gly | Val | Thr | Val | Asp | |
| 200 | | | | | 205 | | | | | 210 | | | | | 215 | |
| AGC | ATC | GGG | ATG | CTG | CCC | CGC | TTC | ATC | CCC | GAG | AAC | CAG | CGC | ACC | GTC | 1008 |
| Ser | Ile | Gly | Met | Leu | Pro | Arg | Phe | Ile | Pro | Glu | Asn | Gln | Arg | Thr | Val | |
| | | | | 220 | | | | | 225 | | | | | 230 | | |
| GCC | GTA | TAC | AGC | TTG | AAG | ATC | GCC | GGG | TGG | CAC | GGG | CCC | AAG | GCC | CCA | 1056 |
| Ala | Val | Tyr | Ser | Leu | Lys | Ile | Ala | Gly | Trp | His | Gly | Pro | Lys | Ala | Pro | |
| | | | 235 | | | | | 240 | | | | | 245 | | | |
| TAC | ACG | AGC | ACC | CTG | CTG | CCC | CCG | GAG | CTG | TCC | GAG | ACC | CCC | AAC | GCC | 1104 |
| Tyr | Thr | Ser | Thr | Leu | Leu | Pro | Pro | Glu | Leu | Ser | Glu | Thr | Pro | Asn | Ala | |
| | | 250 | | | | | 255 | | | | | 260 | | | | |
| ACG | CAG | CCA | GAA | CTC | GCC | CCG | GAA | GAC | CCC | GAG | GAT | TCG | GCC | CTC | TTG | 1152 |
| Thr | Gln | Pro | Glu | Leu | Ala | Pro | Glu | Asp | Pro | Glu | Asp | Ser | Ala | Leu | Leu | |
| | 265 | | | | | 270 | | | | | 275 | | | | | |
| GAG | GAC | CCC | GTG | GGG | ACG | GTG | GCG | CCG | CAA | AGG | AAG | ATC | TTC | CAG | GAC | 1200 |
| Glu | Asp | Pro | Val | Gly | Thr | Val | Ala | Pro | Gln | Arg | Lys | Ile | Phe | Gln | Asp | |
| 280 | | | | 285 | | | | | 290 | | | | | 295 | | |
| GCC | GCG | ACG | CCT | TAC | CAT | CCC | CCG | GCC | ACC | CCG | AAC | AAC | ATG | GGC | CTG | 1248 |
| Ala | Ala | Thr | Pro | Tyr | His | Pro | Pro | Ala | Thr | Pro | Asn | Asn | Met | Gly | Leu | |
| | | | | 300 | | | | | 305 | | | | | | 310 | |
| ATC | GCC | GGC | GCG | GTG | GGC | GGC | AGT | CTC | CTG | GCA | GCC | CTG | GTC | ATT | TGC | 1296 |
| Ile | Ala | Gly | Ala | Val | Gly | Gly | Ser | Leu | Leu | Ala | Ala | Leu | Val | Ile | Cys | |
| | | | 315 | | | | | 320 | | | | | 325 | | | |
| GGA | ATT | GTG | TAC | TGG | ATG | CAC | CGC | CGC | ACT | CGG | AAA | GCC | CCA | AAG | CGC | 1344 |
| Gly | Ile | Val | Tyr | Trp | Met | His | Arg | Arg | Thr | Arg | Lys | Ala | Pro | Lys | Arg | |
| | | 330 | | | | | 335 | | | | | 340 | | | | |
| ATA | CGC | CTC | CCC | CAC | ATC | CGG | GAA | GAC | GAC | CAG | CCG | TCC | TCG | CAC | CAG | 1392 |
| Ile | Arg | Leu | Pro | His | Ile | Arg | Glu | Asp | Asp | Gln | Pro | Ser | Ser | His | Gln | |
| | 345 | | | | | 350 | | | | | 355 | | | | | |

```
CCC TTG TTT TAC TAGATACCCC CCCTTAATGG GTGCGGGGGG GTCAGGTCTG        1444
Pro Leu Phe Tyr
360

CGGGGTTGGG ATGGGACCTT AACTCCATAT AAAGCGAGTC TGGAAGGGGG GAAAGGCGGA   1504

CAGTCGATAA GTCGGTAGCG GGGGACGCGC ACCTGTTCCG CCTGTC                  1550
```

( 2 ) INFORMATION FOR SEQ ID NO:11:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Gly Gly Thr Ala Ala Arg Leu Gly Ala Val Ile Leu Phe Val Val
-25              -20              -15                      -10

Ile Val Gly Leu His Gly Val Arg Gly Lys Tyr Ala Leu Ala Asp Ala
              -5                   1                   5

Ser Leu Lys Met Ala Asp Pro Asn Arg Phe Arg Gly Lys Asp Leu Pro
         10                  15                  20

Val Leu Asp Gln Leu Thr Asp Pro Pro Gly Val Arg Arg Val Tyr His
     25                  30                  35

Ile Gln Ala Gly Leu Pro Asp Pro Phe Gln Pro Pro Ser Leu Pro Ile
 40                  45                  50                  55

Thr Val Tyr Tyr Ala Val Leu Glu Arg Ala Cys Arg Ser Val Leu Leu
             60                  65                      70

Asn Ala Pro Ser Glu Ala Pro Gln Ile Val Arg Gly Ala Ser Glu Asp
             75                  80                  85

Val Arg Lys Gln Pro Tyr Asn Leu Thr Ile Ala Trp Phe Arg Met Gly
         90                  95                 100

Gly Asn Cys Ala Ile Pro Ile Thr Val Met Glu Tyr Thr Glu Cys Ser
        105                 110                 115

Tyr Asn Lys Ser Leu Gly Ala Cys Pro Ile Arg Thr Gln Pro Arg Trp
120                 125                 130                 135

Asn Tyr Tyr Asp Ser Phe Ser Ala Val Ser Glu Asp Asn Leu Gly Phe
             140                 145                 150

Leu Met His Ala Pro Ala Phe Glu Thr Ala Gly Thr Tyr Leu Arg Leu
         155                 160                 165

Val Lys Ile Asn Asp Trp Thr Glu Ile Thr Gln Phe Ile Leu Glu His
        170                 175                 180

Arg Ala Lys Gly Ser Cys Lys Tyr Ala Leu Pro Leu Arg Ile Pro Pro
185                 190                 195

Ser Ala Cys Leu Ser Pro Gln Ala Tyr Gln Gln Gly Val Thr Val Asp
200                 205                 210                 215

Ser Ile Gly Met Leu Pro Arg Phe Ile Pro Glu Asn Gln Arg Thr Val
             220                 225                 230

Ala Val Tyr Ser Leu Lys Ile Ala Gly Trp His Gly Pro Lys Ala Pro
         235                 240                 245

Tyr Thr Ser Thr Leu Leu Pro Pro Glu Leu Ser Glu Thr Pro Asn Ala
         250                 255                 260

Thr Gln Pro Glu Leu Ala Pro Glu Asp Pro Glu Asp Ser Ala Leu Leu
         265                 270                 275

Glu Asp Pro Val Gly Thr Val Ala Pro Gln Arg Lys Ile Phe Gln Asp
280                 285                 290                 295
```

```
Ala Ala Thr Pro Tyr His Pro Pro Ala Thr Pro Asn Asn Met Gly Leu
            300                     305                 310

Ile Ala Gly Ala Val Gly Gly Ser Leu Leu Ala Ala Leu Val Ile Cys
        315                 320                 325

Gly Ile Val Tyr Trp Met His Arg Arg Thr Arg Lys Ala Pro Lys Arg
        330                 335                 340

Ile Arg Leu Pro His Ile Arg Glu Asp Asp Gln Pro Ser Ser His Gln
    345                 350                 355

Pro Leu Phe Tyr
360
```

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

```
TTTTGGATCC  CAAATATGCC  TTGGCGGATG                                       30
```

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GGCGCTGCGG  AATGGTAGTA  GTAGTAGTAA  TTGACGTCTT  TT                       42
```

( 2 ) INFORMATION FOR SEQ ID NO:14:

( i ) SEQUENCE CHARACTERISTICS:
        ( A ) LENGTH: 1635 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 268..1446

( i x ) FEATURE:
        ( A ) NAME/KEY: mat_peptide
        ( B ) LOCATION: 343..1446

( x i ) SEQUENCE DESCRIPTION: SEQ ID NO:14:

```
CTTGGGGGGG  GGGGGGAAGA  AACTAAAAAC  ACATCAAGCC  CACAACCCAT  CCCACAAGGG    60

GGGTTATGGC  GGACCCACCG  CACCACCATA  CTCCGATTCG  ACCACATATG  CAACCAAATC   120

ACCCCCAGAG  GGGAGGTTCC  ATTTTTACGA  GGAGGAGGAG  TATAATAGAG  TCTTTGTGTT   180

TAAAACCCGG  GGTCGGTGTG  GTGTTCGGTC  ATAAGCTGCA  TTGCGAACCA  CTAGTCGCCG   240

TTTTTCGTGT  GCATCGCGTA  TCACGGC ATG GGG CGT TTG ACC TCC GGC GTC          291
                                Met Gly Arg Leu Thr Ser Gly Val
                                -25                         -20

GGG ACG GCG GCC CTG CTA GTT GTC GCG GTG GGA CTC CGC GTC GTC TGC          339
```

-continued

```
Gly Thr Ala Ala Leu Leu Val Val Ala Val Gly Leu Arg Val Val Cys
        -15                 -10                     -5

GCC AAA TAC GCC TTA GCA GAC CCC TCG CTT AAG ATG GCC GAT CCC AAT          387
Ala Lys Tyr Ala Leu Ala Asp Pro Ser Leu Lys Met Ala Asp Pro Asn
      1             5                   10                  15

CGA TTT CGC GGG AAG AAC CTT CCG GTT TTG GAC CAG CTG ACC GAC CCC          435
Arg Phe Arg Gly Lys Asn Leu Pro Val Leu Asp Gln Leu Thr Asp Pro
              20                  25                  30

CCC GGG GTG AAG CGT GTT TAC CAC ATT CAG CCG AGC CTG GAG GAC CCG          483
Pro Gly Val Lys Arg Val Tyr His Ile Gln Pro Ser Leu Glu Asp Pro
          35                  40                  45

TTC CAG CCC CCC AGC ATC CCG ATC ACT GTG TAC TAC GCA GTG CTG GAA          531
Phe Gln Pro Pro Ser Ile Pro Ile Thr Val Tyr Tyr Ala Val Leu Glu
      50                  55                  60

CGT GCC TGC CAC AGC GTG CTC CTA CAT GCC CCA TCG GAG GCC CCC CAG          579
Arg Ala Cys His Ser Val Leu Leu His Ala Pro Ser Glu Ala Pro Gln
  65                  70                  75

ATC GTG CGC GGG GCT TCG GAC GAG GCC CGA AAG CAC ACG TAC AAC CTG          627
Ile Val Arg Gly Ala Ser Asp Glu Ala Arg Lys His Thr Tyr Asn Leu
 80                  85                  90                  95

ACC ATC GCC TGG TAT CGC ATG GGA GAC AAT TGC GCT ATC CCC ATC ACG          675
Thr Ile Ala Trp Tyr Arg Met Gly Asp Asn Cys Ala Ile Pro Ile Thr
             100                 105                 110

GTC ATG GAG TAC ACC GAG TGC CCC TAC AAC AAG TCT TTG GGG GTC TGC          723
Val Met Glu Tyr Thr Glu Cys Pro Tyr Asn Lys Ser Leu Gly Val Cys
         115                 120                 125

CCC ATC CGA ACG CAG CCC CGC TGG AGC TAC TAT GAC AGC TTT AGC GCC          771
Pro Ile Arg Thr Gln Pro Arg Trp Ser Tyr Tyr Asp Ser Phe Ser Ala
     130                 135                 140

GTC AGC GAG GAT AAC CTG GGA TTC CTG ATG CAC GCC CCC GCG TTC GAG          819
Val Ser Glu Asp Asn Leu Gly Phe Leu Met His Ala Pro Ala Phe Glu
 145                 150                 155

ACC GCG GGT ACG TAC CTG CGG CTA GTG AAG ATA AAC GAC TGG ACG GAG          867
Thr Ala Gly Thr Tyr Leu Arg Leu Val Lys Ile Asn Asp Trp Thr Glu
160                 165                 170                 175

ATC ACA CAA TTT ATC CTG GAG CAC CGG GCC CGC GCC TCC TGC AAG TAC          915
Ile Thr Gln Phe Ile Leu Glu His Arg Ala Arg Ala Ser Cys Lys Tyr
             180                 185                 190

GCT CTC CCC CTG CGC ATC CCC CCG GCA GCG TGC CTC ACC TCG AAG GCC          963
Ala Leu Pro Leu Arg Ile Pro Pro Ala Ala Cys Leu Thr Ser Lys Ala
         195                 200                 205

TAC CAA CAG GGC GTG ACG GTC GAC AGC ATC GGG ATG CTC CCC CGC TTT         1011
Tyr Gln Gln Gly Val Thr Val Asp Ser Ile Gly Met Leu Pro Arg Phe
     210                 215                 220

ATC CCC GAA AAC CAG CGC ACC GTC GCC CTA TAC AGC TTA AAA ATC GCC         1059
Ile Pro Glu Asn Gln Arg Thr Val Ala Leu Tyr Ser Leu Lys Ile Ala
 225                 230                 235

GGG TGG CAC GGC CCC AAG CCC CCG TAC ACC AGC ACC CTG CTG CCG CCG         1107
Gly Trp His Gly Pro Lys Pro Pro Tyr Thr Ser Thr Leu Leu Pro Pro
240                 245                 250                 255

GAG CTG TCC GAC ACC ACC AAC GCC ACG CAA CCC GAA CTC GTT CCG GAA         1155
Glu Leu Ser Asp Thr Thr Asn Ala Thr Gln Pro Glu Leu Val Pro Glu
             260                 265                 270

GAC CCC GAG GAC TCG GCC CTC TTA GAG GAT CCC GCC GGG ACG GTG TCT         1203
Asp Pro Glu Asp Ser Ala Leu Leu Glu Asp Pro Ala Gly Thr Val Ser
         275                 280                 285

TCG CAG ATC CCC CCA AAC TGG CAC ATC CCG TCG ATC CAG GAC GTC GCG         1251
Ser Gln Ile Pro Pro Asn Trp His Ile Pro Ser Ile Gln Asp Val Ala
     290                 295                 300

CCG CAC CAC GCC CCC GCC GCC CCC AGC AAC CCG GGC CTG ATC ATC GGC         1299
```

```
Pro   His   His   Ala   Pro   Ala   Ala   Pro   Ser   Asn   Pro   Gly   Leu   Ile   Ile   Gly
      305                     310                           315

GCG   CTG   GCC   GGC   AGT   ACC   CTG   GCG   GCG   CTG   GTC   ATC   GGC   GGT   ATT   GCG         1347
Ala   Leu   Ala   Gly   Ser   Thr   Leu   Ala   Ala   Leu   Val   Ile   Gly   Gly   Ile   Ala
320                           325                           330                           335

TTT   TGG   GTA   CGC   CGC   CGC   GCT   CAG   ATG   GCC   CCC   AAG   CGC   CTA   CGT   CTC         1395
Phe   Trp   Val   Arg   Arg   Arg   Ala   Gln   Met   Ala   Pro   Lys   Arg   Leu   Arg   Leu
                        340                           345                           350

CCC   CAC   ATC   CGG   GAT   GAC   GAC   GCG   CCC   CCC   TCG   CAC   CAG   CCA   TTG   TTT         1443
Pro   His   Ile   Arg   Asp   Asp   Asp   Ala   Pro   Pro   Ser   His   Gln   Pro   Leu   Phe
                  355                           360                           365

TAC   TAGAGGAGTT   TCCCCGTTCC   CGTGTACCTC   TGGGCCCGTG   TGGGAGGGTG                                  1496
Tyr

GCCGGGGTAT   TTGGGTGGGA   CTTGGACTCC   GCATAAAGGG   AGTCTCGAAG   GAGGGAAACT                           1556

AGGACAGTTC   ATAGGCCGGG   AGCGTGGGGC   GCGCACCGCG   TCCCGACGAT   TAGCCACCGC                           1616

GCCCACAGCC   ACCTCGACC                                                                                1635
```

( 2 ) INFORMATION FOR SEQ ID NO:15:

( i ) SEQUENCE CHARACTERISTICS:
        ( A ) LENGTH: 393 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met   Gly   Arg   Leu   Thr   Ser   Gly   Val   Gly   Thr   Ala   Ala   Leu   Leu   Val   Val
-25                           -20                           -15                           -10

Ala   Val   Gly   Leu   Arg   Val   Val   Cys   Ala   Lys   Tyr   Ala   Leu   Ala   Asp   Pro
                        -5                          1                             5

Ser   Leu   Lys   Met   Ala   Asp   Pro   Asn   Arg   Phe   Arg   Gly   Lys   Asn   Leu   Pro
                  10                          15                          20

Val   Leu   Asp   Gln   Leu   Thr   Asp   Pro   Pro   Gly   Val   Lys   Arg   Val   Tyr   His
            25                          30                          35

Ile   Gln   Pro   Ser   Leu   Glu   Asp   Pro   Phe   Gln   Pro   Pro   Ser   Ile   Pro   Ile
40                            45                          50                                55

Thr   Val   Tyr   Tyr   Ala   Val   Leu   Glu   Arg   Ala   Cys   His   Ser   Val   Leu   Leu
                        60                          65                                70

His   Ala   Pro   Ser   Glu   Ala   Pro   Gln   Ile   Val   Arg   Gly   Ala   Ser   Asp   Glu
                  75                          80                          85

Ala   Arg   Lys   His   Thr   Tyr   Asn   Leu   Thr   Ile   Ala   Trp   Tyr   Arg   Met   Gly
            90                          95                          100

Asp   Asn   Cys   Ala   Ile   Pro   Ile   Thr   Val   Met   Glu   Tyr   Thr   Glu   Cys   Pro
      105                         110                         115

Tyr   Asn   Lys   Ser   Leu   Gly   Val   Cys   Pro   Ile   Arg   Thr   Gln   Pro   Arg   Trp
120                           125                         130                               135

Ser   Tyr   Tyr   Asp   Ser   Phe   Ser   Ala   Val   Ser   Glu   Asp   Asn   Leu   Gly   Phe
                        140                         145                         150

Leu   Met   His   Ala   Pro   Ala   Phe   Glu   Thr   Ala   Gly   Thr   Tyr   Leu   Arg   Leu
                  155                         160                         165

Val   Lys   Ile   Asn   Asp   Trp   Thr   Glu   Ile   Thr   Gln   Phe   Ile   Leu   Glu   His
            170                         175                         180

Arg   Ala   Arg   Ala   Ser   Cys   Lys   Tyr   Ala   Leu   Pro   Leu   Arg   Ile   Pro   Pro
      185                         190                         195

Ala   Ala   Cys   Leu   Thr   Ser   Lys   Ala   Tyr   Gln   Gln   Gly   Val   Thr   Val   Asp
200                           205                         210                               215
```

| | | | | | | | | | | | | | |
|---|---|---|---|---|---|---|---|---|---|---|---|---|---|
| Ser | Ile | Gly | Met | Leu<br>220 | Pro | Arg | Phe | Ile | Pro<br>225 | Glu | Asn | Gln | Arg | Thr<br>230 | Val |
| Ala | Leu | Tyr | Ser<br>235 | Leu | Lys | Ile | Ala | Gly<br>240 | Trp | His | Gly | Pro | Lys<br>245 | Pro | Pro |
| Tyr | Thr | Ser<br>250 | Thr | Leu | Leu | Pro | Pro<br>255 | Glu | Leu | Ser | Asp | Thr<br>260 | Thr | Asn | Ala |
| Thr | Gln<br>265 | Pro | Glu | Leu | Val | Pro<br>270 | Glu | Asp | Pro | Glu | Asp<br>275 | Ser | Ala | Leu | Leu |
| Glu<br>280 | Asp | Pro | Ala | Gly | Thr<br>285 | Val | Ser | Ser | Gln | Ile<br>290 | Pro | Pro | Asn | Trp | His<br>295 |
| Ile | Pro | Ser | Ile | Gln<br>300 | Asp | Val | Ala | Pro | His<br>305 | His | Ala | Pro | Ala | Ala<br>310 | Pro |
| Ser | Asn | Pro | Gly<br>315 | Leu | Ile | Ile | Gly | Ala<br>320 | Leu | Ala | Gly | Ser | Thr<br>325 | Leu | Ala |
| Ala | Leu | Val<br>330 | Ile | Gly | Gly | Ile | Ala<br>335 | Phe | Trp | Val | Arg | Arg<br>340 | Arg | Ala | Gln |
| Met | Ala<br>345 | Pro | Lys | Arg | Leu | Arg<br>350 | Leu | Pro | His | Ile | Arg<br>355 | Asp | Asp | Asp | Ala |
| Pro<br>360 | Pro | Ser | His | Gln | Pro<br>365 | Leu | Phe | Tyr | | | | | | | |

We claim:

1. A method for inhibiting the infection of susceptible cells by herpes simplex virus comprising contacting said cells with a composition comprising a variant herpes simplex virus glycoprotein D molecule comprising amino acids 1 to 300 of SEQ ID NO: 2 and an acceptable carrier.

2. A method for inhibiting the infection of susceptible cells by herpes simplex virus comprising contacting said cells with a composition comprising a variant herpes simplex virus glycoprotein D molecule comprising amino acids −2 to 300 of SEQ ID NO: 2 and an acceptable carrier.

3. A method for inhibiting the infection of susceptible cells by herpes simplex virus comprising contacting said cells with a composition comprising a variant herpes simplex virus glycoprotein D molecule comprising amino acids 1 to 306 of SEQ ID NO: 2 and an acceptable carrier.

4. A method for inhibiting the infection of susceptible cells by herpes simplex virus comprising contacting said cells with a composition comprising the gD-1(Δ290–299t) molecule (amino acids −2 to 306 of SEQ ID NO: 2) and an acceptable carrier.

* * * * *

UNITED STATES PATENT AND TRADEMARK OFFICE
CERTIFICATE OF CORRECTION

PATENT NO. : 5,814,486
DATED : September 29, 1998
INVENTOR(S) : Cohen, et. al.

It is certified that error appears in the above-identified patent and that said Letters Patent is hereby corrected as shown below:

Column 1, line 19 replace "simplex virus" with --*simplex virus*--;

Column 6, line 3 replace "GGAAGATCTTCC" with --GGAAGATCTTCC--;

Column 6, line 20 replace "AAGCTT" with --AAGCTT--;

Column 6, line 26 replace "GGAAGATCTTCC" with --GGAAGATCTTCC--;

Column 6, line 35 replace "AAGCTT" with --AAGCTT--;

Column 7, line 4 replace "GGATCC" with --GGATCC--;

Column 7, line 8 replace "GTAGTAGTAGTAGTA" with --GTAGTAGTAGTAGTA--;

Column 7, line 9 replace "GACGTC" with --GACGTC--;

Column 11, line 5 replace "- - -" with -- -- --;

Column 11, line 50 replace "Δ299" with --Δ290--;

Column 12, line 48 replace "Balb c" with --Balb/c--;

Signed and Sealed this

Fourteenth Day of December, 1999

Attest:

Q. TODD DICKINSON

*Attesting Officer*   *Acting Commissioner of Patents and Trademarks*